(12) United States Patent
Etrych et al.

(10) Patent No.: US 8,603,990 B2
(45) Date of Patent: Dec. 10, 2013

(54) GRAFTED MACROMOLECULAR CONJUGATES OF DOXORUBICIN WITH ANTICANCER ACTIVITY AND METHOD OF THEIR PREPARATION

(75) Inventors: Tomas Etrych, Klinec (CZ); Petr Chytil, Prague (CZ); Karel Ulbrich, Prague (CZ); Tomas Mrkvan, Holesov (CZ); Blanka Rihova, Prague (CZ)

(73) Assignee: Zentiva k.s., Prague (CS)

( * ) Notice: Subject to any disclaimer, the term of this patent is extended or adjusted under 35 U.S.C. 154(b) by 1121 days.

(21) Appl. No.: 12/441,619

(22) PCT Filed: Sep. 18, 2007

(86) PCT No.: PCT/CZ2007/000087
§ 371 (c)(1),
(2), (4) Date: Aug. 25, 2009

(87) PCT Pub. No.: WO2008/034391
PCT Pub. Date: Mar. 27, 2008

(65) Prior Publication Data
US 2009/0306004 A1    Dec. 10, 2009

(30) Foreign Application Priority Data
Sep. 18, 2006 (CZ) ............................... PV 2006-592

(51) Int. Cl.
A61K 31/704 (2006.01)
C07K 1/113 (2006.01)
C07H 15/252 (2006.01)
A61P 35/00 (2006.01)

(52) U.S. Cl.
USPC ............................... 514/34; 530/345; 536/6.4

(58) Field of Classification Search
None
See application file for complete search history.

(56) References Cited

U.S. PATENT DOCUMENTS 7,279,318 B1 * 10/2007 Seymour et al. ............ 435/235.1

FOREIGN PATENT DOCUMENTS

EP          1 782 833        5/2007
WO    WO 2005/007798    *  1/2005

OTHER PUBLICATIONS

Zheng-Rong Lu et al. Functionalized Semitelechelic Poly[N-2-hydroxypropyl)methyacrylamide] for Protein Modification. Bioconjugate Chemistry vol. 9, No. 6, Nov. 1988 pp. 793-804.*

Etrych et al. "Synthesis of HMPA Copolymers Containing Doxorubicin Bound via Hydrazone Linkage. Effect of Spacer on Drug Release and in vitro Cytotoxicity." Macromol. Biosci vol. 2, 2002, pp. 43-52.*
XP 008088087, Polymers Containing Enzymatically Degradable Bonds, 8a), Degradation of Oligopeptide Sequences in N-2(s-hydroxypropyl)methacrylamide Copolymers by Bovine, Spleen Cathespin B, Pavla Rejmanova et al., Makromol. Chem. 184, No. 11, Nov. 1983 pp. 2009-2020.
XP008076237, Synthesis of HMPA Copolymers Containing Doxorubicin Bound via a Hydrazone Linkage. Effect of Spacer on Drug Release and in vitro Cytotoxicity, Tomas Etrych et al.,—Macromol. Biosci vol. 2, 2002, pp. 43-52.
XP008088088, Polymers Containing Enzymatically Degradable Bonds, 4a, Preliminary Experiments in Vivo, Jindrich Kopecek et al.,—Macromol. Chem 182 No. 11, Nov. 1981 pp. 2941-2949.
XP-002467297, Soluble, crosslinked N-(2-Hydroxypropyl)methacrylamide copolymers as potential drug carriers, Susan A. Cartlidge et al., Journal of controlled release 1987 Netherlands, vol. 3, No. 1, 1986, pp. 55-66.
XP-002467298, The Dawning Era of Polymer Therapeutics, Ruth Duncan, Nature Reviews Drug Discovery, vol. 2, May 2003 vol. 2, No. 5 pp. 347-360.
XP008088074, Nanoscale polymer carriers to deliver chemotherapeutic agents to tumors, Mateja Cegnar et al.,—Expert Opin. Biol. Ther. (2005) vol. 5 No. 12 pp. 1557-1569.
High-molecular weight HPMA copolymer-adriamycin conjugates, M. Dvorak, P. Kopeckova et al., Aug. 5, 1999, Journal of controlled release vol. 60, No. 2-3 pp. 321-332.
XP-002467296, Soluble, crosslinked N-(2-Hydroxypropyl)methacrylamide copolymers as potential drug carriers, Susan A. Cartlidge et al., Journal of controlled release 1987 Netherlands, vol. 4, No. 4, 1987, pp. 253-264.
XP008054938, Functionalized Semitelechelic Poly[N-2-hydroxphropyl)methacrylamide] for Protein Modification, Zheng-Rong Lu et al., Bioconjugate Chemistry vol. 9, No. 6, Nov. 1988 pp. 793-804.

* cited by examiner

Primary Examiner — Robert A Wax
Assistant Examiner — Danah Al-Awadi
(74) Attorney, Agent, or Firm — Pearl Cohen Zedek Latzer, LLP

(57) ABSTRACT

A polymeric drug, in which a cancerostatic connected via spacers containing hydrolytically cleavable hydrazone bonds is bound to a water-soluble polymeric carrier prepared on the basis of a N-(2-hydroxypropyl)methacrylamide copolymer, wherein the structure of the polymeric drug consists of the main chain of N-(2-hydroxypropyl)methacrylamide carrying the cancerostatic and another chain of N-(2-hydroxypropyl) methacrylamide—a graft, which may also carry a cancerostatic, said grafts being bound to the main chain by a bond that is stable in the body and/or by a bond cleavable in the body, especially by an oligopeptide spacer selected from the series of GlyLeuGly (SEQ ID. NO. 1), GlyPheGly (SEQ ID. NO. 2), GlyPheLeuGly (SEQ ID. NO. 3) and GlyLeuPheGly (SEQ ID. NO. 4), and a method of its preparation.

6 Claims, 4 Drawing Sheets

```
SEQUENCE LISTING

<160> NUMBER OF SEQ ID NOS: 4

<210> SEQ ID NO 1
<211> LENGTH: 3
<212> TYPE: PRT
<213> ORGANISM: Artificial Sequence
<220> FEATURE:
<223> OTHER INFORMATION: Oligopeptide

<400> SEQUENCE: 1

Gly Leu Gly
1

<210> SEQ ID NO 2
<211> LENGTH: 3
<212> TYPE: PRT
<213> ORGANISM: Artificial Sequence
<220> FEATURE:
<223> OTHER INFORMATION: Oligopeptide

<400> SEQUENCE: 2

Gly Phe Gly
1

<210> SEQ ID NO 3
<211> LENGTH: 4
<212> TYPE: PRT
<213> ORGANISM: Artificial Sequence
<220> FEATURE:
<223> OTHER INFORMATION: Oligopeptide

<400> SEQUENCE: 3

Gly Phe Leu Gly
1

<210> SEQ ID NO 4
<211> LENGTH: 4
```

```
<212> TYPE: PRT
<213> ORGANISM: Artificial Sequence
<220> FEATURE:
<223> OTHER INFORMATION: Oligopeptide

<400> SEQUENCE: 4

Gly Leu Phe Gly
1
```

GRAFTED MACROMOLECULAR CONJUGATES OF DOXORUBICIN WITH ANTICANCER ACTIVITY AND METHOD OF THEIR PREPARATION

CROSS-REFERENCE TO RELATED APPLICATIONS

This application is a National Phase Application of PCT International Application No. PCT/CZ2007/000087, International Filing Date Sep. 18, 2007, claiming priority of Czech Republic Patent Application, PV 2006-592, filed Sep. 18, 2006 which is incorporated herein by reference in its entirety.

TECHNICAL FIELD

This invention concerns macromolecular water-soluble polymeric carriers of cancerostatics that allow for targeted transport of cytostatics, especially doxorubicin (DOX), into solid tumors and ensure the elimination of the polymer from the body. The effect of the conjugate of a polymeric carrier and a cancerostatic drug is focused on targeted therapy of tumor diseases in human medicine.

BACKGROUND ART

The latest trends of drug development are focused on such drug forms that enable targeted therapy of a biologically active substance, preferentially at the site of the required therapeutic effect. Target effect drugs are primarily utilized in such areas where side effects of the active component may potentially cause damage to any healthy parts of the body. This danger is most relevant in cytostatic therapy. Polymeric substances, especially water-soluble polymers, used as drug carriers offer an important possibility of solving the problem. The attachment of a cytostatic to a water-soluble polymer through a chemical bond enables significant increase in solubility of insoluble or slightly soluble drugs, substantially decreasing their toxicity. The high molecular weight of polymers protects the drug from a quick elimination from the body by glomerular filtration enabling an extended circulation in the blood, as well as greater biological efficiency of the drug. Besides, macromolecular substances, especially synthetic polymers, may accumulate in solid tumors due to the EPR (enhanced permeability and retention) effect [Maeda 2000, 2001]. If a cancerostatic is bound to a macromolecular carrier, this fact may be used for its targeted accumulation in the tumor. A great number of systems that are based on this principle have been developed. Polymeric micelles are one of them. They represent a carrier system which is structurally different from soluble polymers developed to achieve tumor specific transport of cytostatics to solid tumors, they also take advantage of the EPR effect of firm tumors to increase accumulation of the macromolecular drug in the tumor but they are usually prepared by arranging amphiphilic diblock copolymers into macromolecular micellic formations creating colloid solutions. In the micelles, the drug is usually bound to the micellic hydrophobic core by physical (hydrophobic interactions, ionic bonds) or covalent bonds [Kataoka 2001, Yokoyama 1999, Bae 2003, Yoo 2002, Bronich 1999]. If the drug is to be released from the micelle the chemical bond needs to be broken and, at the same time, the hydrophobic interactions in the micellic core disintegrated. This is especially true for hydrophobic drugs. On the other hand, in soluble systems that accumulate in solids tumors the macromolecules are dissolved in the aqueous environment on a molecular basis and the molecule usually takes the shape of a random coil. The drug is then in contact with a hydrophilic polymer and to be released it does not have to overcome the barrier of hydrophobic interactions. Polymeric conjugates of cancerostatics with soluble polymers have been prepared and studied in which the drug with an anticancer effect was bound to the polymer by a non-cleavable covalent bond, hydrolytically unstable ionic bond or by a covalent bond susceptible to enzymatic or simple chemical hydrolysis. Such systems are capable of releasing the cancerostatic from the carrier in its active form either in the tumor or, more specifically, directly in the tumor cell. A significant group of such drugs is formed by polymeric drugs based on copolymers of N-(2-hydroxypropyl)methacrylamide (HPMA), a number of which is actively targeted to tumors through a directing structure attached to the polymer (antibodies, hormones) [Duncan 1985, Rihova 2000, Kopecek 2001, 2000]. However, their synthesis is rather complicated. References quote much information on the preparation and studies of properties of polymers carrying a cancerostatic attached to the polymer by a bond susceptible to hydrolysis in an aqueous environment. [Kratz 1999]. A significant role among them is also played by HPMA copolymers carrying the doxorubicin cancerostatic bound to the polymeric chain by a hydrolytically cleavable hydrazone bond [Etrych 2002, Ulbrich 2004a, Ulbrich 2004b, Ulbrich—patents]. This bond is relatively stable in the bloodstream environment (during the transport in the body) and hydrolytically unstable in a slightly acid environment of a living cell. The rate of hydrolysis of this bond controls the rate of drug release and whence the concentration of the active substance at the site of required effect. Both in vitro and in vivo tests in mice revealed that these polymeric cancerostatics showed significantly higher anticancer effect against a number of tumor lines in comparison with a free drug and in a number of cases their application resulted in a total cure of tested animals even in a therapeutic mode of administration [Rihova 2001, Etrych 2001]. The major problem associated with the application of HPMA copolymers is their non-cleavable carbon chain; therefore the area of molecular weights that can be used for the preparation of the polymeric carrier is limited to molecular weights smaller than 40,000 to 50,000, i.e. below the exclusion limit of the body. Polymers of a higher molecular weight cannot be effectively and sufficiently eliminated from the body and their application would lead to their excessive accumulation in the body. To achieve an efficient EPR effect, i.e. significant accumulation in tumors, polymers, including HPMA copolymers, with a molecular weight high above the exclusion limit need to be used (Seymour 1995, Noguchi 1998). Therefore, it is convenient for the molecular weight of the polymeric carrier to be high enough but, at the same time, to ensure for the degradation of the polymer after the active component is released into fragments that can be excluded from the body by, e.g. glomerular filtration. This invention suggests and demonstrates the efficiency of a macromolecular polymeric drug with a defined and biodegradable carrier skeleton that allows for the transport of the cytostatic into the tumor as well as subsequent exclusion of the polymeric carrier from the body.

DISCLOSURE OF INVENTION

The essence of the polymeric drug according to this invention lies in the fact that the doxorubicin cancerostatic, attached to the polymeric chains by spacers containing pH-sensitive hydrolytically cleavable hydrazone bonds, is bound to a water-soluble polymeric carrier prepared on the basis of a HPMA copolymer. Such spacers may be formed by single amino acids, oligopeptides or by any other structures that enable their termination by a hydrazide group. The structure of the polymeric drug is selected to consist of the main polymeric chain formed by a HPMA copolymer carrying doxorubicin bound by a hydrazone bond through a spacer to which other chains of a HPMA homopolymer or copolymer also carrying doxorubicin bound via a hydrazone bond are grafted. The drugs according to this invention are characterized by the fact that the polymeric grafts are attached to the main chain either by a bond stable in the body or by bonds cleavable in the body, preferably by bonds cleavable in the targeted tumor cell, e.g. by an enzymatically cleavable oligopeptide sequence or by a reductively cleavable disulfide bond. The molecular weight of the main chain is selected below the exclusion limit of the body, preferably ranging from 10,000 to 50,000 g/mol; molecular weights of the polymeric grafts range from 5,000 to 50,000 g/mol. Enzymatically degradable oligopeptide sequences preferably contain the GlyLeuGly (SEQ ID. NO. 1), GlyPheGly (SEQ ID. NO. 2), GlyPheLeuGly (SEQ ID. NO. 3) or GlyLeuPheGly (SEQ ID. NO. 4) oligopeptide sequences, the reductively cleavable bonds contain disulfide structures of various composition. The molecular weights of the polymeric grafts and of the main chain are selected so that both the main chain alone before bonding the grafts and the separate grafts are excludable from the body, preferably by glomerular filtration. The molecular weight of the grafted polymer is then high, exceeding the exclusion limit of the body and ensuring an extended circulation time and sufficient EPR effect, as well as capture in the tissue of solid tumors. The molecular weights of the new grafted conjugates of doxorubicin may not only be controlled by the molecular weight of the basic polymer and the grafts but also by the ratio of the number of grafts per one main chain. The molecular weight of such a grafted polymer preferably ranges from 50,000 to 400,000 g/mol; the content of doxorubicin both in the main chain and in the grafts ranges from 1 to 25% by weight (0.3 to 8 mol %).

The polymeric drug according to this invention should be administered primarily intravenously (injection or infusion) but it may also be administered intratumorally or intraperitoneally. The polymer with a chemically bound cytostatic is stable during circulation in the bloodstream; the hydrazone bond between doxorubicin and the polymer is relatively stable under the physiological conditions of the bloodstream (pH 7.4). After extravasation and capture in solid tumors due to the EPR effect the molecularly solved conjugate penetrates to each tumor cell by pinocytosis and as a result of the decrease in pH from the outer pH 7.4 to the intracellular pH 5 to 6 the hydrazone bond should be hydrolyzed and the cytostatic released in the target cell which should activate its cytotoxic effect. In the slightly acid reductive environment of the cell (references quote concentrations of glutathione in the living cells cytoplasm ranging from 1 to 5 mmol) hydrolysis-controlled release of the drug and reduction of disulfide bonds should occur, as well as disintegration of the macromolecular grafted polymer to the original polymeric fragments excludable from the body. Similar degradation of the carrier should occur in a carrier containing grafts bound by enzymatically cleavable oligopeptide sequences. This degradation of the polymeric skeleton should be caused by the action of lysosomal cellular enzymes. Objectivity of the mechanism of action of polymeric drugs according to his invention as suggested above is demonstrated by experiments involving model release of doxorubicin from the polymeric chain as well as polymer degradation experiments carried out in the physiological environment modeling the situation in a living cell. The results of such tests, including anticancer activity tests, are given in the examples section of this application.

Synthesis and Structures of Polymeric Conjugates

The polymeric conjugates according to this invention are synthesized in several steps; a detailed final structure of a conjugate significantly depends on the selected synthetic approach.

In the first synthetic step the basic monomers are synthesized: HPMA, methacryloylated derivatives of amino acids and oligopeptides terminated with the 4-nitrophenoxy (ONp) or thiazolidine-2-thione (TT) group, methacryloylated derivatives of amino acids and oligopeptides terminated with the hydrazide ($NHNH_2$) group, or terminated with the hydrazide group protected by t.-butyloxycarbonyl group (Boc), or terminated with doxorubicin, bound via a hydrazone bond and methacryloylated macromonomers prepared by methacryloylation of HPMA of a semitelechelic copolymer terminated with the primary amino group ($NH_2$).

In the second step polymeric precursors are synthesized, i.e. random HPMA copolymers serving as the main chain and semitelechelic polymers with terminal reactive groups serving for grafting of the main polymeric chain.

The main polymeric chain carrying functional groups along it, such as 4-nitrophenoxy, thiazolidine-2-thione groups, hydrazide groups, primary amino groups, sulfhydryl (SH) groups or dithiopyridyl (PDS) groups, may be prepared either by radical copolymerization of the above functional monomers with HPMA or by polymeranalogous transformation of the basic copolymer carrying the functional groups.

The basic copolymer is a copolymer of HPMA and methacryloylated hydrazides of amino acids or oligopeptides, the essence of which is the content of 70 to 98 mol % HPMA and 2 to 30% mol units with functional groups. The below structural schemes introduce two abbreviations for spacers in the side copolymer chains: i) $SP_1$ is the aminoacyl in methacryloyl(aminoacyl)-hydrazides and methacryloyl(aminoacyl) amines, e.g. glycyl, glycylglycyl, β-alanyl, 6-aminohexanoyl (AH), 4-aminobenzoyl, or a combined acyl derived from oligopeptides such as GlyPheGly (SEQ ID. NO. 2), GlyLeuGly (SEQ ID. NO. 1), GlyLeuPheGly (SEQ ID. NO. 4) or SEQ ID. NO. 3; ii) $SP_2$ is a combined acyl in methacryloyl(aminoacyl)hydrazides and methacryloyl(aminoacyl) amines derived from an enzymatically degradable oligopeptide sequence preferably containing oligopeptide sequences GlyLeuGly (SEQ ID. NO. 1), GlyPheGly (SEQ ID. NO. 2), GlyPheLeuGly (SEQ ID. NO. 3) or GlyLeuPheGly (SEQ ID. NO. 4).

The following random copolymers with monomeric units as described above may be prepared by copolymerizations or polymeanalogous reactions:

Copolymers 1:

These copolymers carry reactive 4-nitrophenoxy or acylthiazolidine-2-thione groups along the chain.

Radical copolymerization resulted in the preparation of the HPMA terpolymer with methacryloylated amino acids or oligopeptides terminated with a Boc-protected hydrazide group and with a methacryloylated biodegradable oligopeptide (e.g. GlyPheLeuGly (SEQ ID. NO. 3)) terminated by the 4-nitrophenoxy (Copolymer 1a) or thiazolidine-2-thione groups (Copolymer 1b).

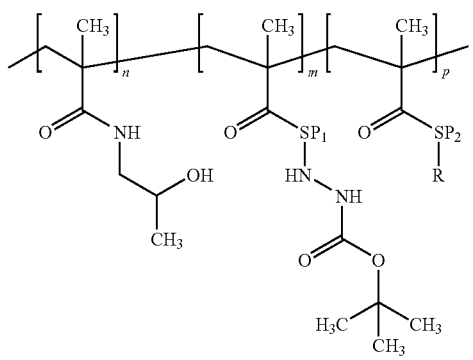

Copolymer 1a, 1b structural scheme

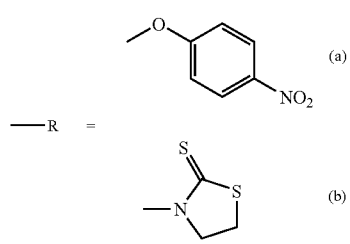

Copolymers 2:

These copolymers carry reactive hydrazide or primary amino groups along the chain. Radical copolymerization of HPMA with methacryloylated amino acids or oligopeptides terminated by a hydrazide group resulted in the preparation of Copolymer 2a.

Copolymer 2a structural scheme

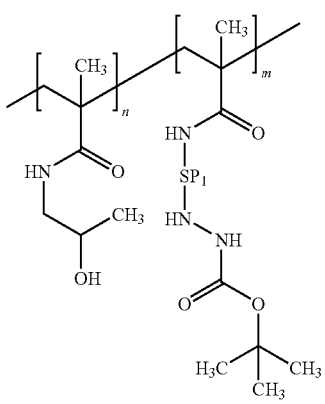

Radical copolymerization resulted in the preparation of the HPMA terpolymer with methacryloylated amino acids or oligopeptides terminated by a Boc-protected hydrazide group and with a methacryloylated biodegradable oligopeptide (e.g. GlyPheLeuGly (SEQ ID. NO. 3)) terminated by a hydrazide group (Copolymer 2b)

Copolymer 2b structural scheme

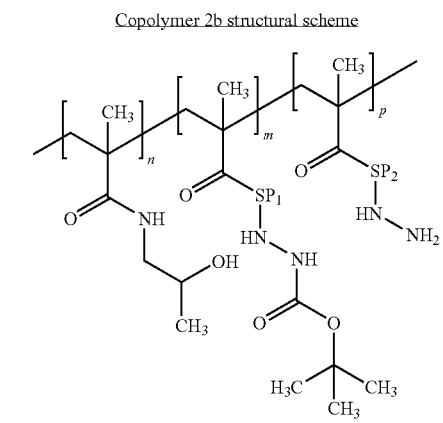

Copolymer 2c was prepared by a polymeranalogous reaction using Copolymer 1a and 1b. A random copolymer carrying reactive hydrazide or primary amino groups along its chain was prepared in the reaction of 4-nitrophenyl ester (Copolymer 1a) or acylthiazolidine-2-thione groups (Copolymer 1b) with an excess of hydrazine hydrate, ethylene diamine, butylene diamine or hexamethylene diamine.

Copolymer 2c structural scheme

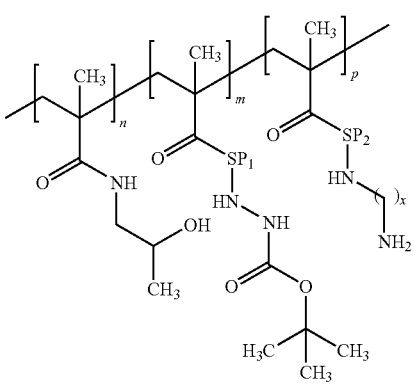

$x = 0, 2, 4, 6$

Copolymers 3:

These random copolymers carry reactive dithiopyridyl groups along the chain. After the protective group was removed a polymeranalogous reaction of copolymer 2a and N-succinimidyl-[3-(2-pyridyldithio)]propionate (SPDP) (generally, any bifunctional agent with an activated carboxyl group and pyridyldisulfide group, such as SPDP, 4-succinimidyloxycarbonyl-α-methyl-α-(2-pyridyldithio)toluene, N-succininnidyl-[4-(2-pyridyldithio)]butyrate, N-(2-sulfosuccinimidyl-[3-(2-pyridyldithio)]propionate) resulted in the preparation of the HPMA terpolymer with methacryloylated amino acids or oligopeptides terminated by a hydrazide group and with methacryloylated amino acids or oligopeptides terminated by N-[3-(2-pyridyldithio)propionyl]ethylamide group. (Copolymer 3a)

Copolymer 3a structural scheme

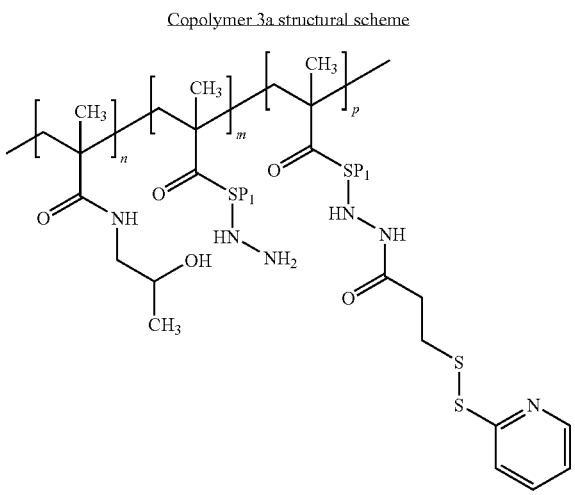

A polymeranalogous reaction of copolymers 2b and 2c with N-succinimidyl-[3-(2-pyridyldithio)]propionate (SPDP) resulted in the preparation of the HPMA terpolymer with methacryloylated amino acids or oligopeptides terminated by a Boc-protected hydrazide group and with a methacryloylated biodegradable oligopeptide (e.g. GlyPheLeuGly (SEQ ID. NO. 3)) terminated by the N-[3-(2-pyridyldithio)propiony]ethylamide group. (Copolymer 3b)

Copolymer 3b structural scheme

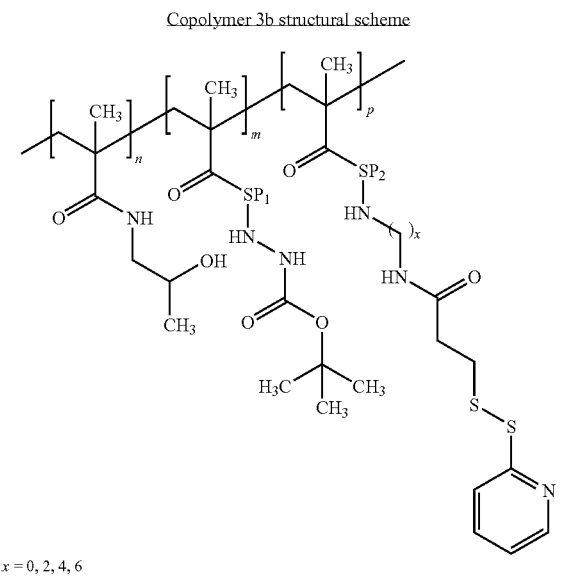

x = 0, 2, 4, 6

A polymeranalogous reaction of copolymers 1a and 1b with 2-(2-pyridyldithio)ethylamine (PDEA) (generally, any bifunctional agent with a primary amino or hydrazide group and pyridyldisulfide group, such as PDEA, 2-(2-pyridyldithio)ethylhydrazine, 4-(2-pyridyldithio)butylamine) resulted in the preparation of the HPMA terpolymer with methacryloylated amino acids or oligopeptides terminated by a Boc-protected hydrazide group and with a methacryloylated biodegradable oligopeptide (e.g. GlyPheLeuGly (SEQ ID. NO. 3)) terminated by the 2-(2-pyridyldithio)ethylamide group. (Copolymer 3c).

Copolymer 3c structural scheme

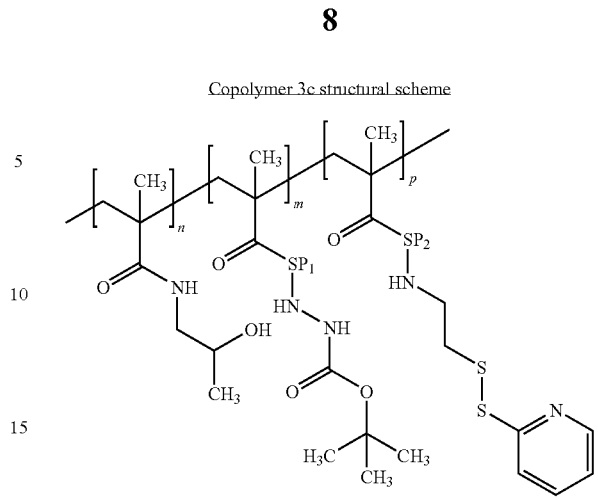

Copolymers 4:

These random copolymers carry reactive sulfhydryl groups along the chain.

After the protective group was removed a polymer-analogous reaction of copolymer 2a and 2-imino-thiolate (ITH) resulted in the preparation of the HPMA terpolymer with methacryloylated amino acids or oligopeptides terminated by a hydrazide group and with methacryloylated amino acids or oligopeptides terminated by the 4-sulfanylbutaneimidohydrazide group. (Copolymer 4a)

Copolymer 4a structural scheme

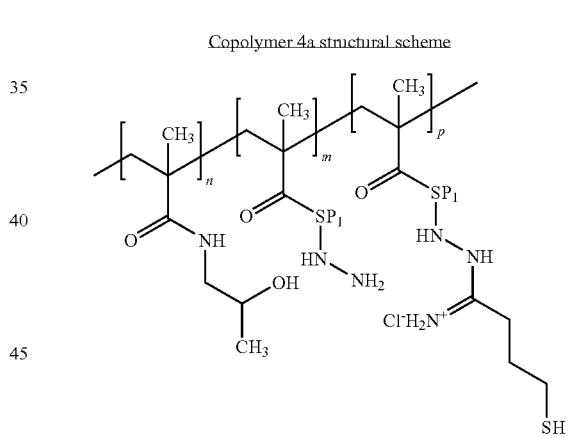

A polymeranalogous reaction of copolymers 2b and 2c with 2-imino-thiolate (ITH) resulted in the preparation of the HPMA terpolymer with methacryloylated amino acids or oligopeptides terminated by a Boc-protected hydrazide group and with a methacryloylated oligopeptide (e.g. GlyPheLeuGly (SEQ ID. NO. 3)) terminated by the 4-sulfanylbutaneimideamide group. (Copolymer 4b)

Copolymer 4b structural scheme

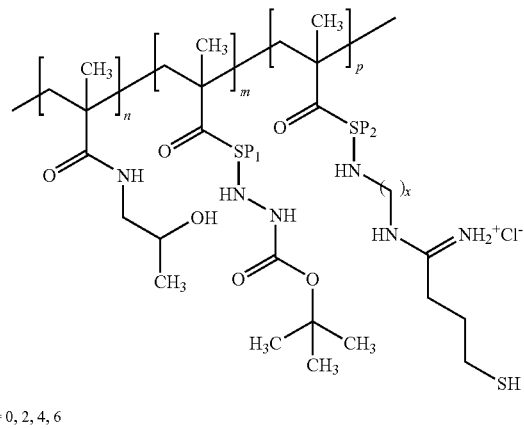

x = 0, 2, 4, 6

A polymeranalogous reaction of copolymers 3a with dithiothreitol (DTT) resulted in the preparation of the HPMA terpolymer HPMA with methacryloylated amino acids or oligopeptides terminated by a hydrazide group and with methacryloylated amino acids or oligopeptides terminated by the 3-sulfanylpropanohydrazide group (Copolymer 4c).

Copolymer 4c structural scheme

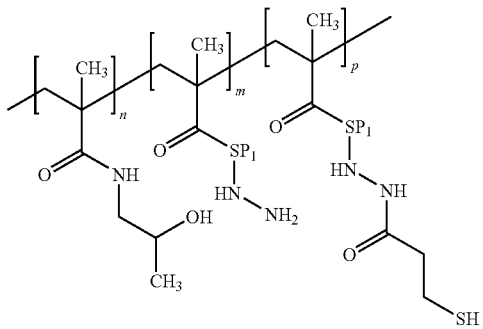

A polymeranalogous reaction of copolymers 3b and 3c with dithiothreitol (DTT) resulted in the preparation of the HPMA terpolymer with methacryloylated amino acids or oligopeptides terminated by a Boc-protected hydrazide group and with a methacryloylated oligopeptide (e.g. GlyPheLeuGly (SEQ ID. NO. 3)) terminated by the 3-sulfanylpropaneamide (Copolymer 4d) or 2-sulfanylethylamine group (Copolymer 4e).

Copolymer 4d, 4e structural scheme

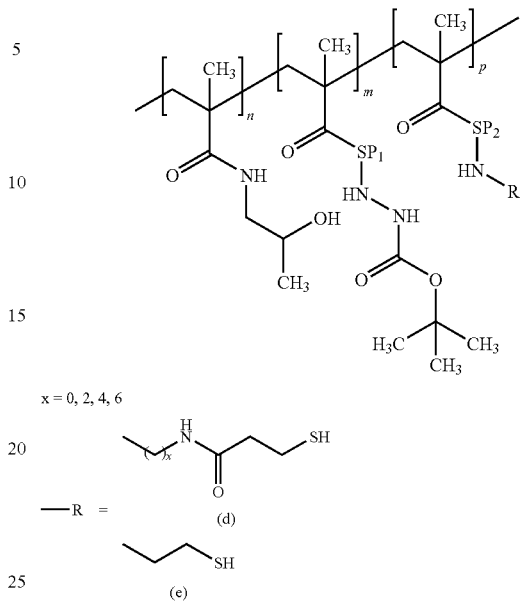

x = 0, 2, 4, 6

Semitelechelic copolymers are characterized by the content of 85 to 99 mol % HPMA, 1 to 15% mol units of methacryloylated Boc-protected hydrazides of amino acids or oligopeptides and by a reactive group situated at the end of the polymeric chain. These polymers were prepared by radical copolymerization carried out in the presence of a chain transfer agent [sulfanylpropionic acid (SPA) or cysteamine], under initiation by the 3,3'-azo-bis(4-cyanoisovaleric acid) (ABIA) azoinitiator or by the 3,3'-[4,4'-azobis(4-cyano-4-methyl-1-oxo-butane-4,1-diyl)]bis(thiazolidine-2-thione) (ABIA-TT) reactive azoinitiator. The following semitelechelic copolymers were prepared as grafts for the preparation of grafted copolymers by copolymerization and modification of the terminal functional groups:

Structural scheme of ABIA-TT

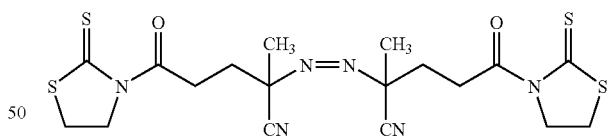

Grafts 1:

This group of polymers includes semitelechelic copolymers containing terminal reactive N-succinimidyl ester or acylthiazolidine-2-thione groups.

Radical polymerization of HPMA initiated by the ABIA-TT initiator resulted in the preparation of the HPMA homopolymer with a terminal reactive acylthiazolidine-2-thione group (Graft 1a).

Graft 1a structural scheme

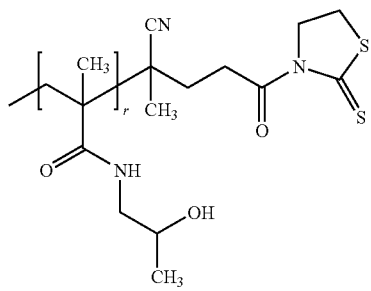

An HPMA copolymer with methacryloylated amino acids or oligopeptides terminated by a Boc-protected hydrazide group was prepared by radical HPMA polymerization carried out in the presence of the SPA transfer agent. The copolymer is terminated by an N-succinimidyl ester group. (Graft 1b).

Graft 1b structural scheme

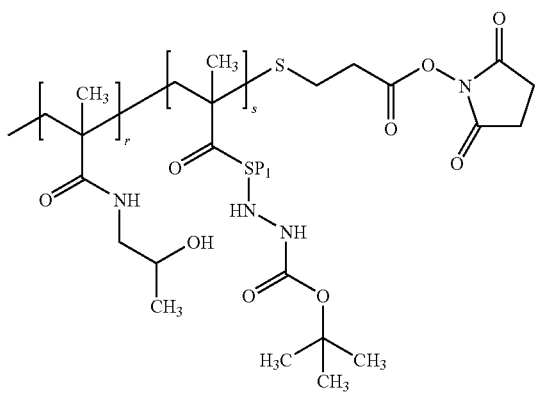

An HPMA copolymer with methacryloylated amino acids or oligopeptides terminated by a Boc-protected hydrazide group and terminal acylthiazolidine-2-thione group was prepared by radical copolymerization of respective monomers under initiation by ABIA-TT. A copolymer with a terminal N-succinimidyl ester group was prepared analogously under initiation by ABIA and with subsequent activation of the terminal carboxyl group by N-hydroxysuccinimide (Graft 1c).

Graft 1c structural scheme

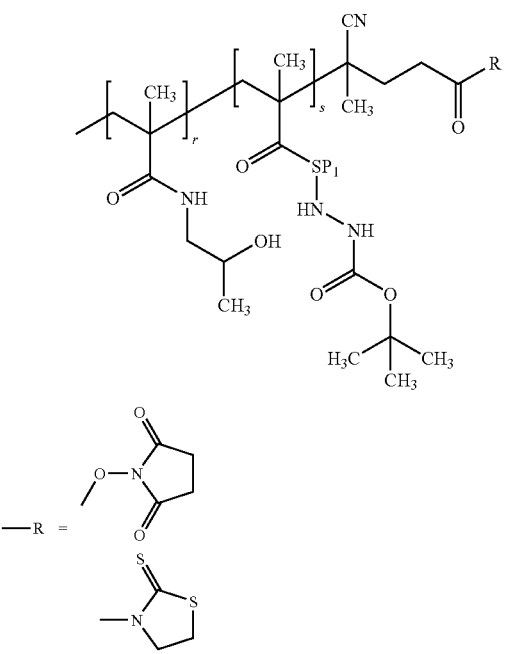

An HPMA copolymer with methacryloylated amino acids or oligopeptides terminated by a Boc-protected hydrazide group and with a terminal N-succinimidyl ester of a biodegradable oligopeptide (e.g. GlyPheLeuGly (SEQ ID. NO. 3), terminated by N-Hydroxysuccinimide ester), generally $SP_2$, (Graft 1d) was prepared by radical HPMA copolymerization with relevant monomers initiated by ABIA, followed by activation of the terminal carboxyl group by N-hydroxysuccinimide.

Graft 1d structural scheme

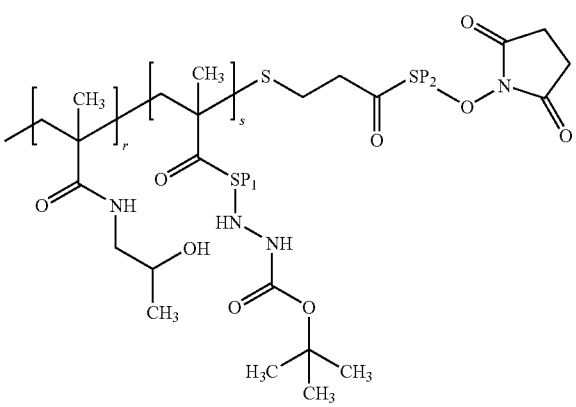

Grafts 2:

These semitelechelic copolymers contain terminal reactive hydrazide or primary amino groups. An HPMA copolymer with methacryloylated amino acids or oligopeptides terminated by a Boc-protected hydrazide group was prepared by radical copolymerization carried out in the presence of cysteamine. This copolymer terminates by a primary amino group. (Graft 2a)

Graft 2a structural scheme

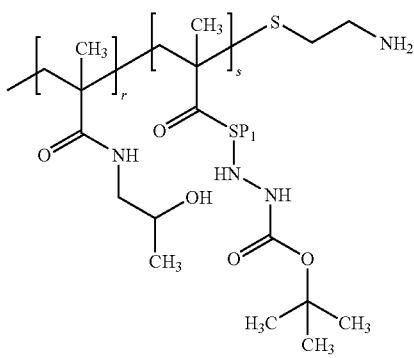

An HPMA copolymer with methacryloylated amino acids or oligopeptides terminated by a Boc-protected hydrazide group terminated by an amino acid was prepared in a reaction of terminal activated carboxyl groups of Grafts 1b and 1c in the excess of hydrazine hydrate, ethylene diamine, butylene diamine or hexamethylene diamine (Graft 2b).

Graft 2b structural scheme

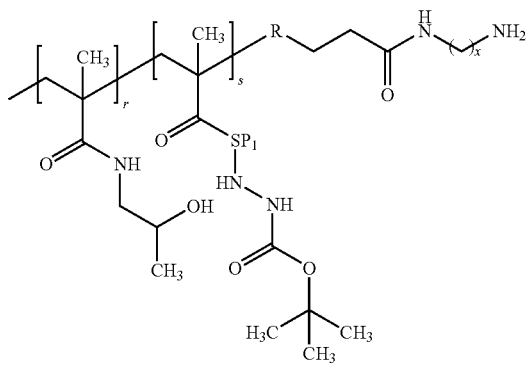

x = 0, 2, 4, 6

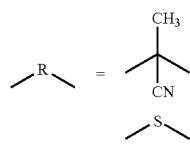

Grafts 3:

These semitelechelic copolymers contain terminal reactive dithiopyridyl groups.

An HPMA copolymer with methacryloylated amino acids or oligopeptides terminated by a Boc-protected hydrazide group terminated by the 2-(2-pyridyldithio)ethylamide group was prepared in a reaction of the terminal reactive groups of grafts 1b and 1c with PDEA. (Graft 3a).

Graft 3a structural scheme

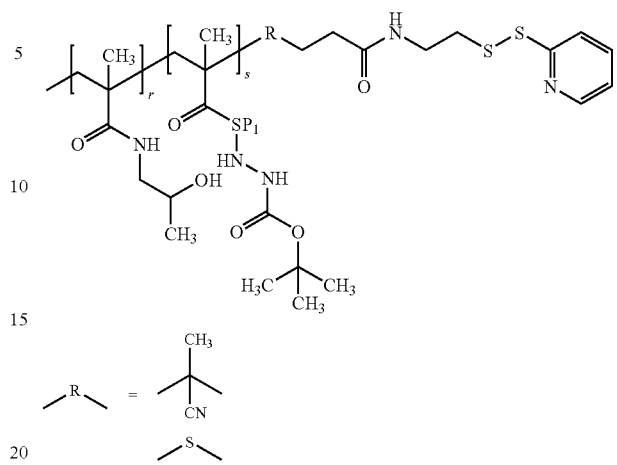

An HPMA copolymer with methacryloylated amino acids or oligopeptides terminated by a Boc-protected hydrazide group terminated by the N-[3-(2-pyridyldithio)propionyl] amide group was prepared in a reaction of the terminal reactive groups of grafts 2a and 2b with SPDP (Graft 3b).

Graft 3b structural scheme

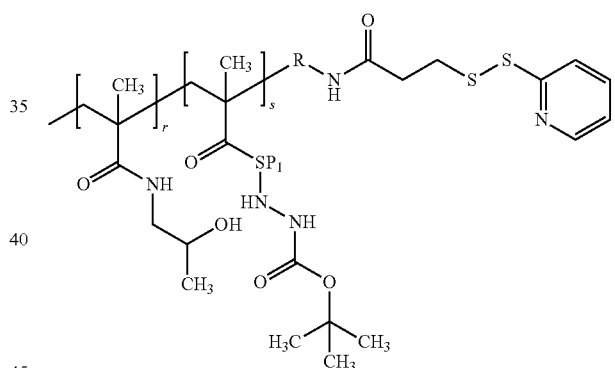

x = 0, 2, 4, 6

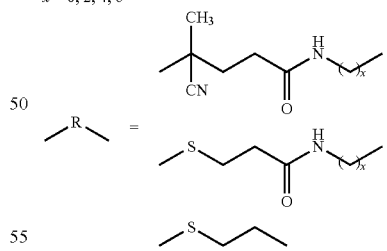

Grafts 4:

These semitelechelic copolymers contain terminal reactive sulfhydryl groups.

An HPMA copolymer with methacryloylated amino acids or oligopeptides terminated by a Boc-protected hydrazide group was prepared in a reaction of grafts 2a and 2b with ITH. The polymeric chain of this copolymer terminates with the 4-sulfanylbutaneimideamide or 4-sulfanylbutaneimidohydrazide group (Graft 4a).

Graft 4a structural scheme

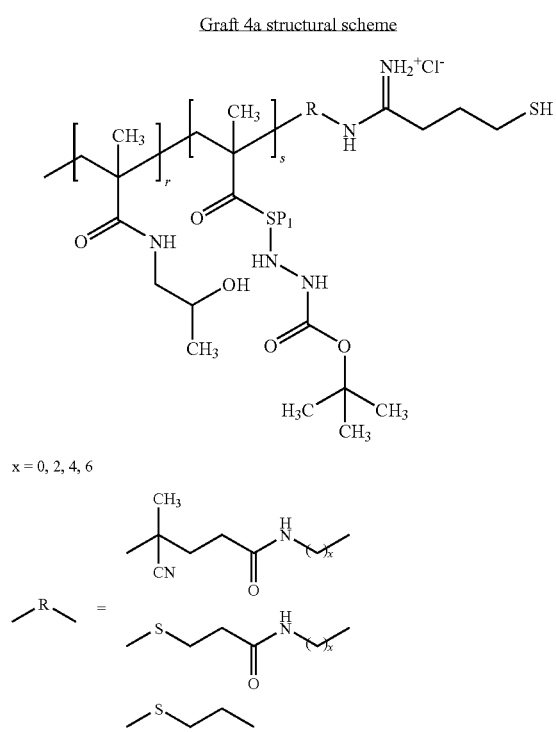

x = 0, 2, 4, 6

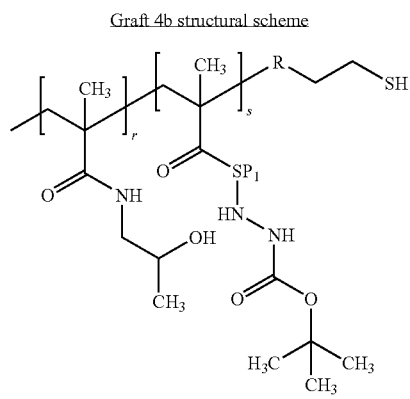

An HPMA copolymer with methacryloylated amino acids or oligopeptides terminated by a Boc-protected hydrazide group was prepared in a reaction of grafts 3a and 3b with DTT. The chain of this copolymer terminates with the 3-sulfanylpropanohydrazide, 3-sulfanylpropaneamide or 2-sulfanylethylamine groups (Graft 4b).

Graft 4b structural scheme

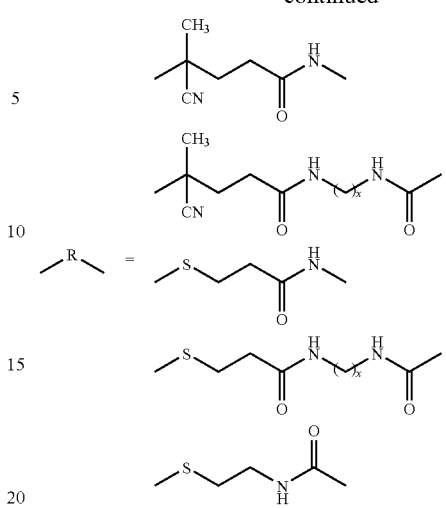

Polymeric carrier and polymeric conjugate. The polymeric carrier is a grafted macromolecular polymer without the drug bound to it, prepared by a grafting reaction of a semitelechelic copolymer to the basic copolymer, as shown in the examples section. The above-mentioned copolymers whose hydrazide group is protected by the Boc group (t.-butyloxycarbonyl) are predominantly used for the reactions. In the last stage of conjugate synthesis the protective group is removed from the hydrazide group and the conjugate is bound to doxorubicin via a hydrazone bond in a reaction in methanol under catalyzed by the acetic acid. The final polymeric drug (the conjugate) is purified by precipitation and, if needed, by column chromatography as shown in the examples section.

The subject of this patent involves polymeric conjugates of doxorubicin whose detailed structures are shown in the scheme section and whose synthesis is described in the examples section.

With regard to the type of the groups reacting in the basic polymers and semitelechelic grafts the polymeric conjugates are further divided into 5 basic groups. The following conjugates were prepared:

Conjugates 1

These conjugates carry DOX bound to the polymer via a hydrazone bond; the grafts are bound to the main chain by a non-degradable bond. Copolymers carrying hydrazide or primary amino groups along their main chain and semitelechelic copolymers with the terminal N-succinimidyl ester or acylthiazolidine-2-thione groups were used for the preparation of these polymeric conjugates.

Conjugate 1a was prepared by the reaction of the hydrazide groups of Copolymer 2a with the acylthiazolidine-2-thione groups of Graft 1a, followed by deprotection of the hydrazide groups and linking DOX to the polymer.

Conjugate 1a structural scheme

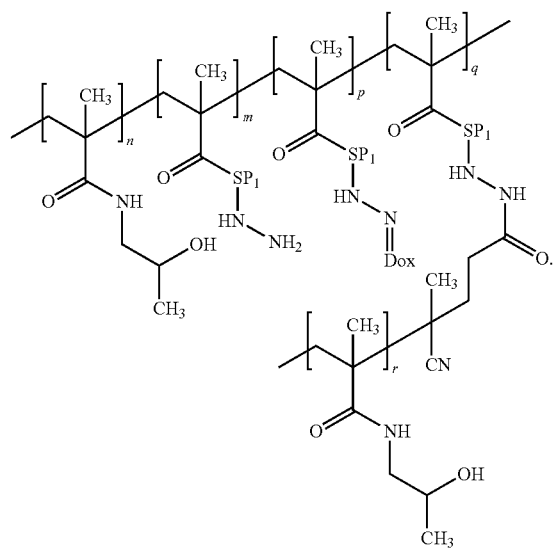

(n = 40-335, m = 0-85, p = 1-20, q = 1-10, r = 34-350)

Conjugate 1b was prepared by the reaction of the hydrazide groups of Copolymer 2a with the thiazolidine-2-thione or N-succinimidyl groups of Graft 1b or 1c, followed by deprotection of the hydrazide groups and linking DOX to the polymer.

Conjugate 1b structural scheme

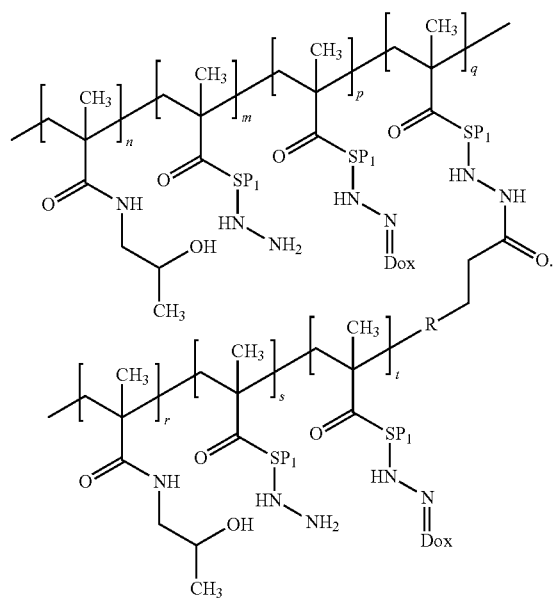

(n = 40-335, m = 0-85, p = 1-20, q = 1-10, r = 34-350, s = 0-50, t = 1-20)

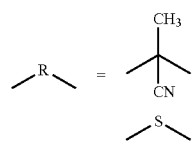

Conjugate 1c was prepared by the reaction of the hydrazide groups of Copolymer 2a with the N-succinimidyl ester groups of Graft 1d, followed by deprotection of the hydrazide groups and linking DOX to the polymer.

Conjugate 1c structural scheme

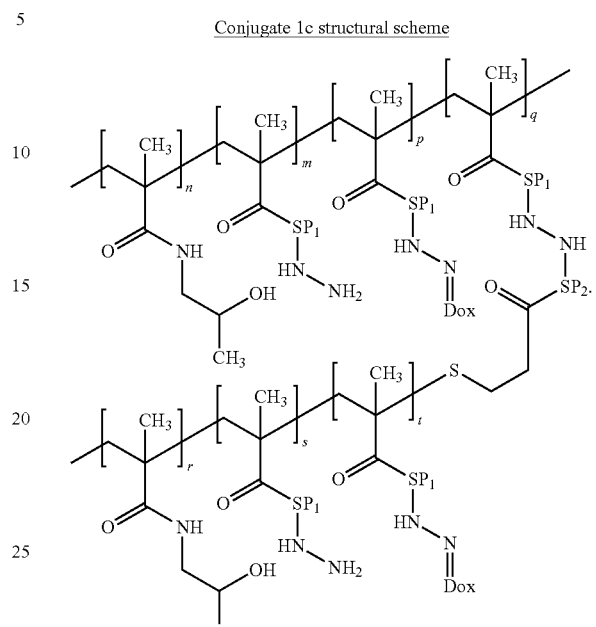

(n = 40-335, m = 0-85, p = 1-20, q = 1-10, r = 34-350, s = 0-50, t = 1-20)

Conjugate 1d was prepared by the reaction of the hydrazide or primary amino groups of Copolymer 2b or 2c with the acylthiazolidine-2-thione or N-succinimidyl ester groups of Graft 1b or 1c, followed by deprotection of the hydrazide groups and linking DOX to the polymer.

Conjugate 1d structural scheme

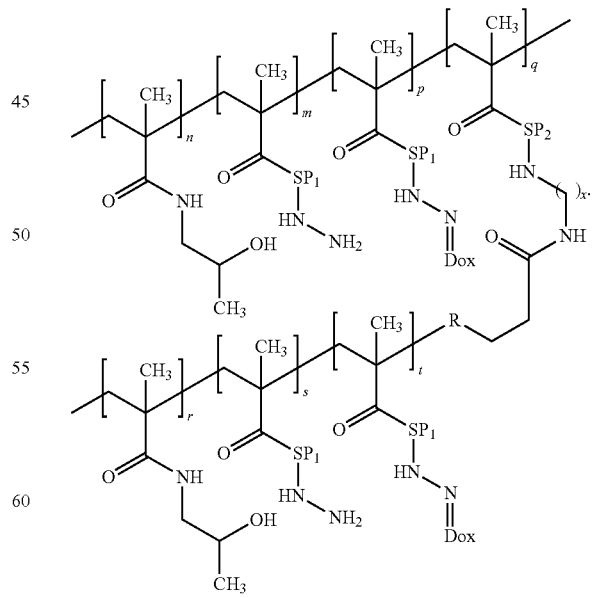

-continued ($n = 40\text{-}335, m = 0\text{-}85, p = 1\text{-}20, q = 1\text{-}10, r = 34\text{-}350, s = 0\text{-}50, t = 1\text{-}20$)
$x = 0, 2, 4, 6$

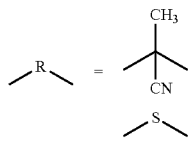

Conjugates 2

These conjugates carry DOX bound to the polymer via a hydrazone bond; the grafts are bound to the main chain by a biodegradable bond—an enzymatically cleavable oligopeptide sequence. Copolymers carrying 4-nitrophenoxy or thiazolidine-2-thione groups along their main chain and semitelechelic copolymers with terminal hydrazide or primary amino groups were used for the preparation of these polymeric conjugates.

Conjugate 2 was prepared by the reaction of the acylthiazolidine-2-thione or 4-nitrophenyl ester groups of Copolymer 1a or 1b with the hydrazide or primary amino groups of Graft 2a or 2b, followed by deprotection of the hydrazide groups and linking DOX to the polymer.

Conjugate 2 structural scheme

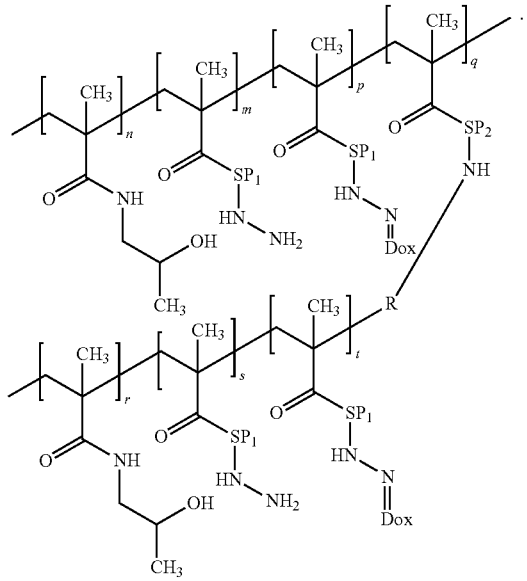

($n = 40\text{-}335, m = 0\text{-}85, p = 1\text{-}20, q = 1\text{-}10, r = 34\text{-}350, s = 0\text{-}50, t = 1\text{-}20$)
$x = 0, 2, 4, 6$

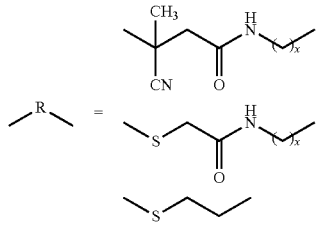

Conjugates 3

These conjugates carry DOX bound to the polymer via a hydrazone bond; the grafts are bound to the main chain by a biodegradable bond—disulfide bridges reductively cleavable in the target cells cytoplasm. Copolymers carrying reactive dithiopyridyl groups along their main chain and semitelechelic copolymers with terminal sulfhydryl groups were used for the preparation of these polymeric conjugates.

Conjugate 3a was prepared by the reaction of the dithiopyridyl groups of Copolymer 3a or 3b with the sulfhydryl groups of Graft 4a or 4b, followed by deprotection of the hydrazide groups and linking DOX to the polymer.

Conjugate 3 structural scheme

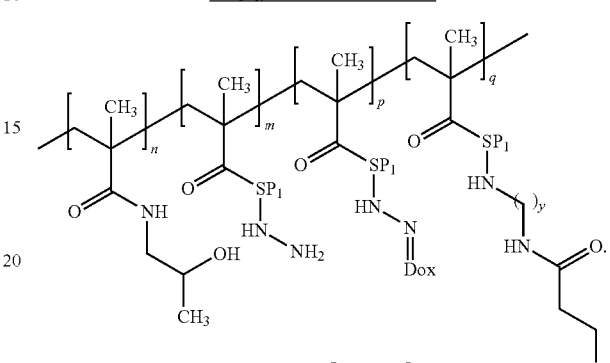

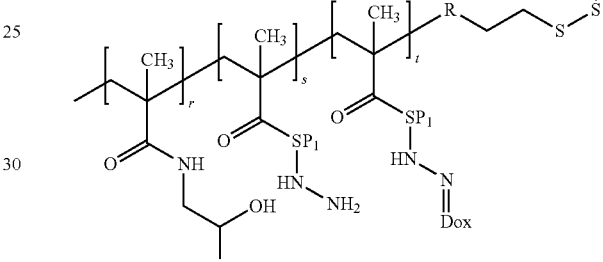

-continued ($n = 40-335, m = 0-85, p = 1-20, q = 1-10, r = 34-350, s = 0-50, t = 1-20$)
$x = 0, 2, 4, 6$
$y = 0, 2, 4, 6$

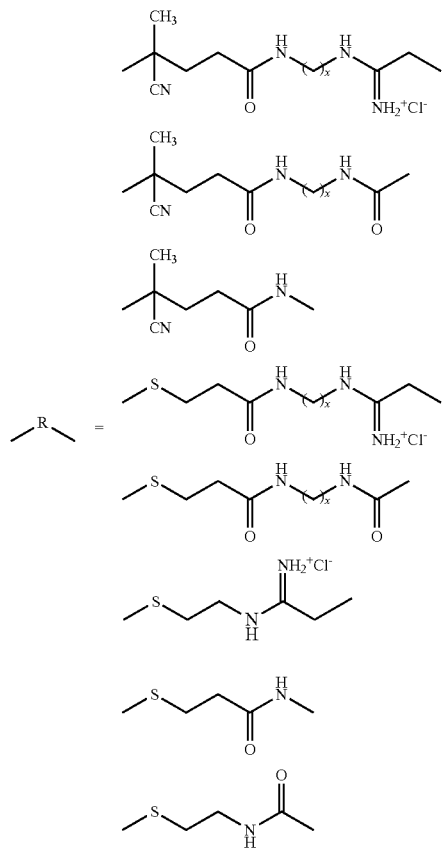

Conjugate 3b was prepared by the reaction of the dithiopyridyl groups of Copolymer 3c with the sulfhydryl groups of Graft 4a or 4b, followed by deprotection of the hydrazide groups and linking DOX to the polymer.

Conjugate 3b structural scheme

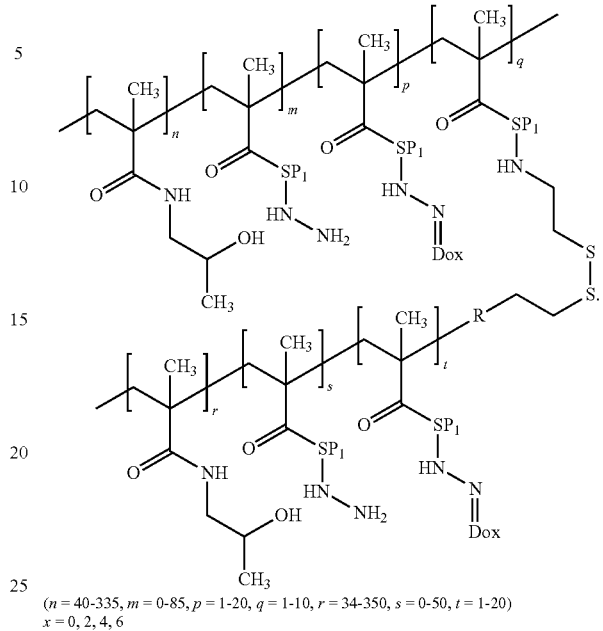

($n = 40-335, m = 0-85, p = 1-20, q = 1-10, r = 34-350, s = 0-50, t = 1-20$)
$x = 0, 2, 4, 6$

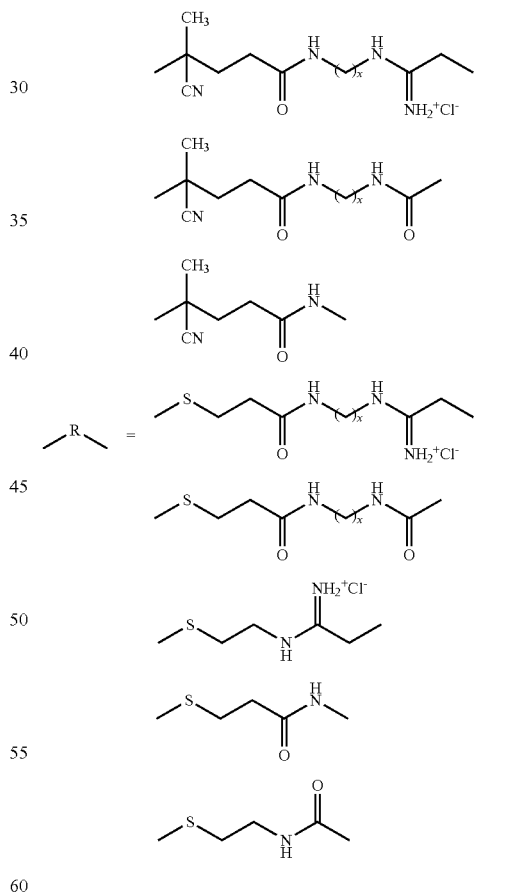

Conjugates 4

These conjugates carry DOX bound to the polymer via a hydrazone bond; the grafts are bound to the main chain by a biodegradable bond—disulfide bridges reductively cleavable in the target cells cytoplasm. Copolymers carrying sulfhydryl groups along their main chain and semitelechelic copolymers with terminal reactive dithiopyridyl groups were used for the preparation of these polymeric conjugates.

Conjugate 4a was prepared by the reaction of the sulfhydryl groups of Copolymer 4a or 4b with the dithiopyridyl groups of Graft 3a or 3b, followed by deprotection of the hydrazide groups and linking DOX to the polymer.

Conjugate 4a structural scheme

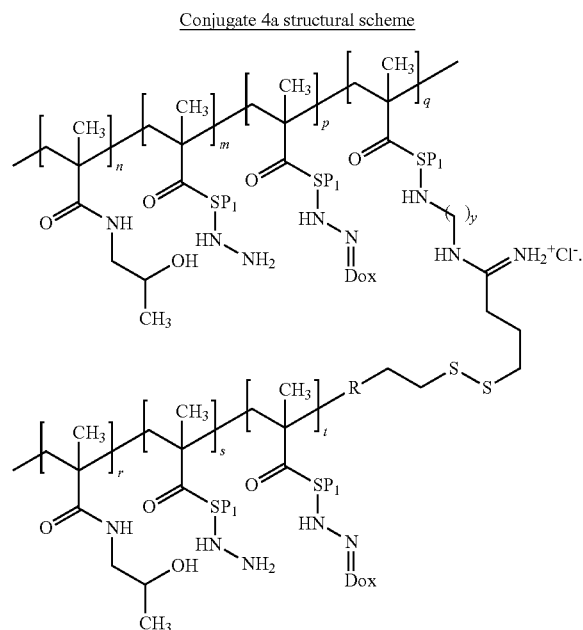

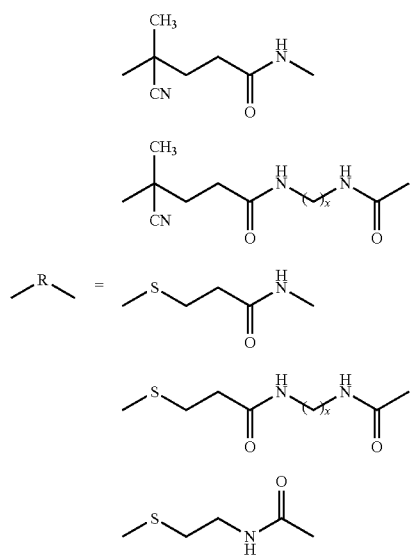

($n = 40\text{-}335, m = 0\text{-}85, p = 1\text{-}20, q = 1\text{-}10, r = 34\text{-}350, s = 0\text{-}50, t = 1\text{-}20$)
$x = 0, 2, 4, 6$
$y = 0, 2, 4, 6$ Conjugate 4b was prepared by the reaction of the sulfhydryl groups of Copolymer 4c or 4d with the dithiopyridyl groups of Graft 3a or 3b, followed by deprotection of the hydrazide groups and linking DOX to the polymer.

Conjugate 4b structural scheme

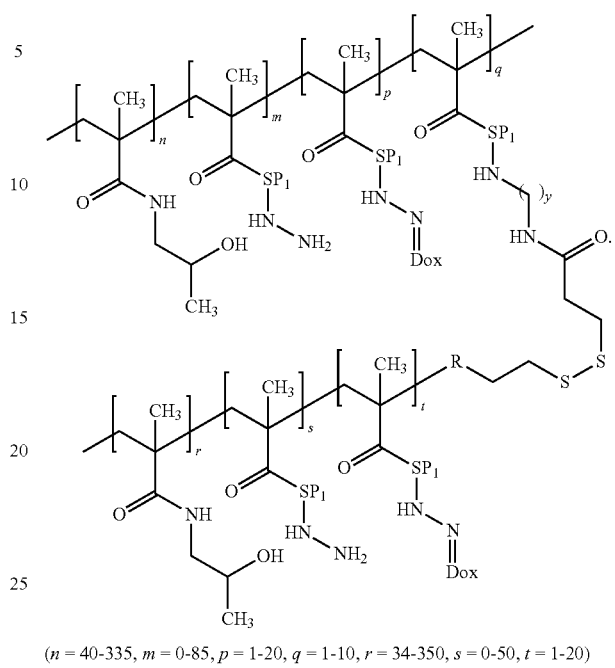

($n = 40\text{-}335, m = 0\text{-}85, p = 1\text{-}20, q = 1\text{-}10, r = 34\text{-}350, s = 0\text{-}50, t = 1\text{-}20$)
$x = 0, 2, 4, 6$
$y = 0, 2, 4, 6$

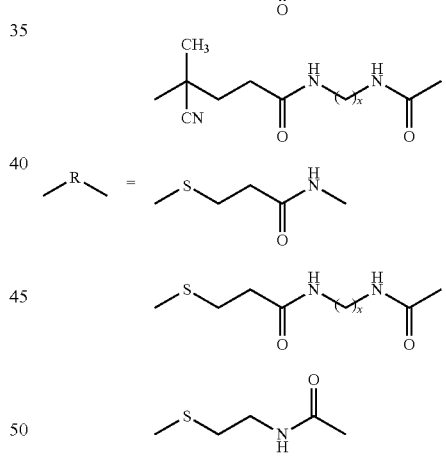

Conjugate 4c was prepared by the reaction of the sulfhydryl groups of Copolymer 4e with the dithiopyridyl groups of Graft 3a or 3b, followed by deprotection of the hydrazide groups and linking DOX to the polymer.

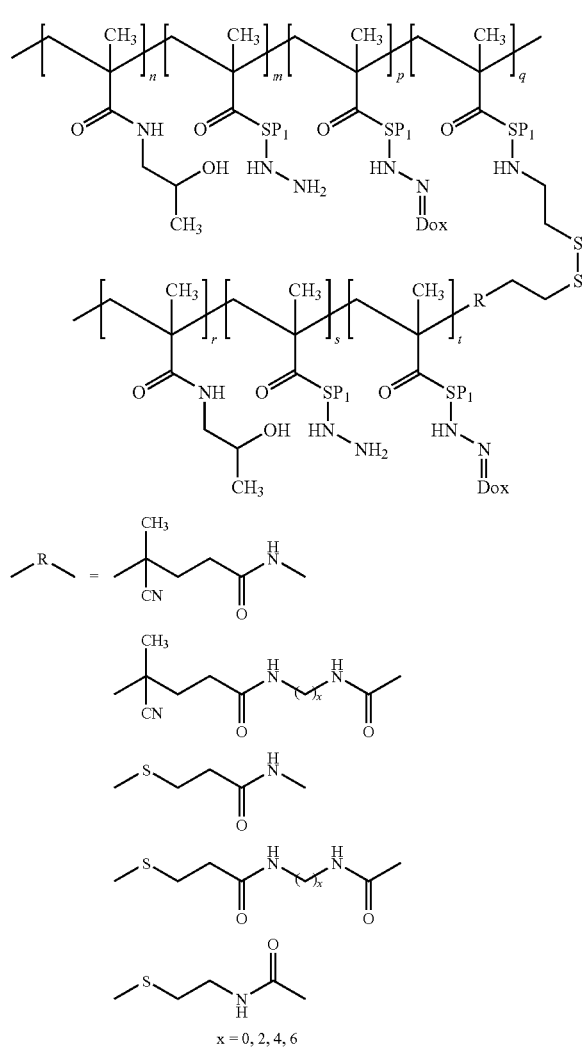

Conjugate 4c structural scheme (n = 40-335, m = 0-85, p = 1-20, q = 1-10, r = 34-350, s = 0-50, t = 1-20).

Conjugates 5

These conjugates carry DOX bound to the polymer via a hydrazone bond; the grafts are bound to the main chain by a biodegradable bond—enzymatically cleavable oligopeptide sequence. They were prepared by radical terpolymerization of HPMA with methacryloylated amino acids or oligopeptides terminated by a Boc-protected hydrazide group and methacryloylated macromonomers prepared by methacryloylation of HPMA of a semitelechelic copolymer terminated by a primary amino group (Macromonomers, FIG. 32). The macromonomers were prepared in the reaction of the hydrazide or primary amino groups of Grafts 2a and 2b with methacryloylated derivatives of biodegradable oligopeptides terminated by the 4-nitrophenoxy or thiazolidine-2-thione group.

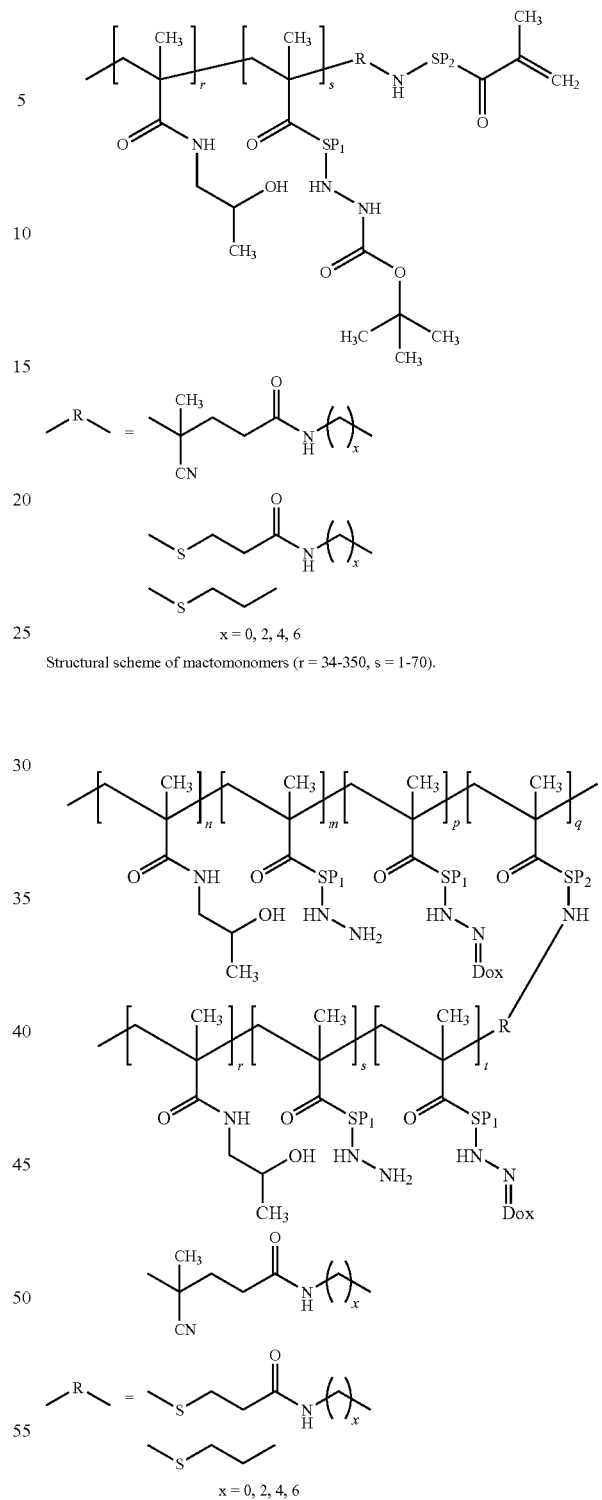

Structural scheme of mactomonomers (r = 34-350, s = 1-70).

Conjugate 5 structural scheme (n = 40-335, m = 0-85, p = 1-20, q = 1-10, r = 34-350, s = 0-50, t = 1-20).

Figure 1:
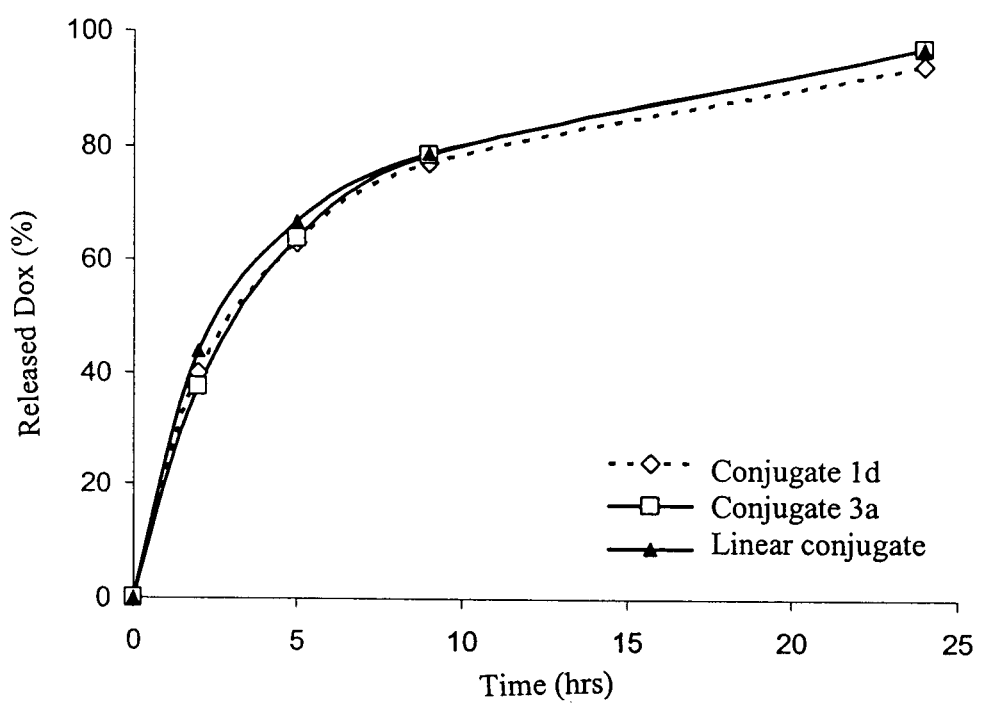
FIG. 1 shows a graph of release rate of DOX from grafted polymeric conjugates and the linear polymeric conjugate in pH 5 buffer (intracellular environment model).
Figure 2:
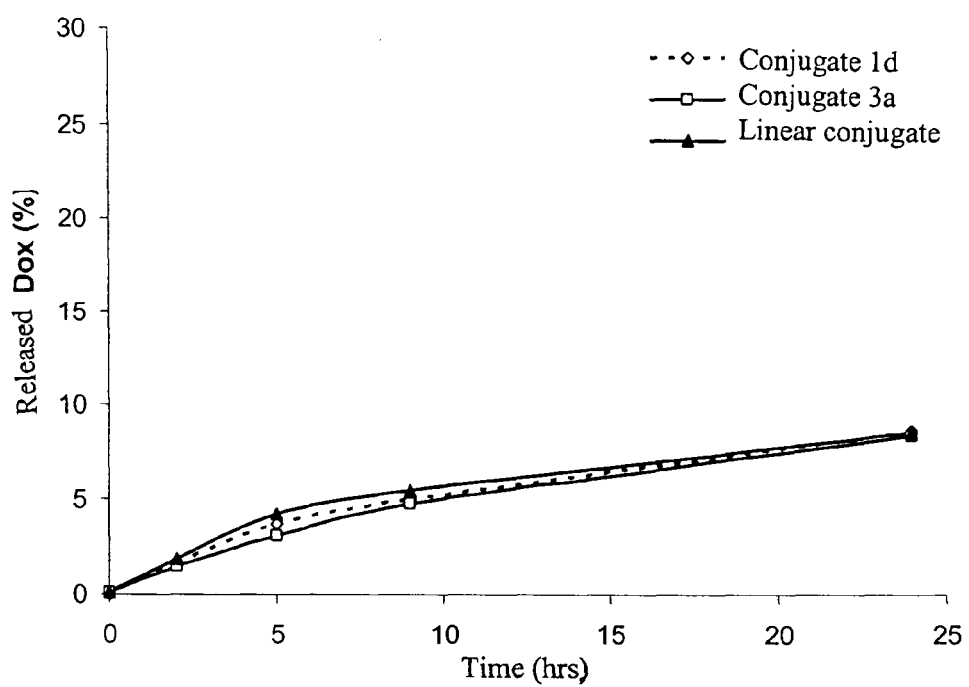
FIG. 2 shows a graph of release rate of DOX from grafted polymeric conjugates and the linear polymeric conjugate in pH 7.4 buffer (bloodstream model).
Figure 3:
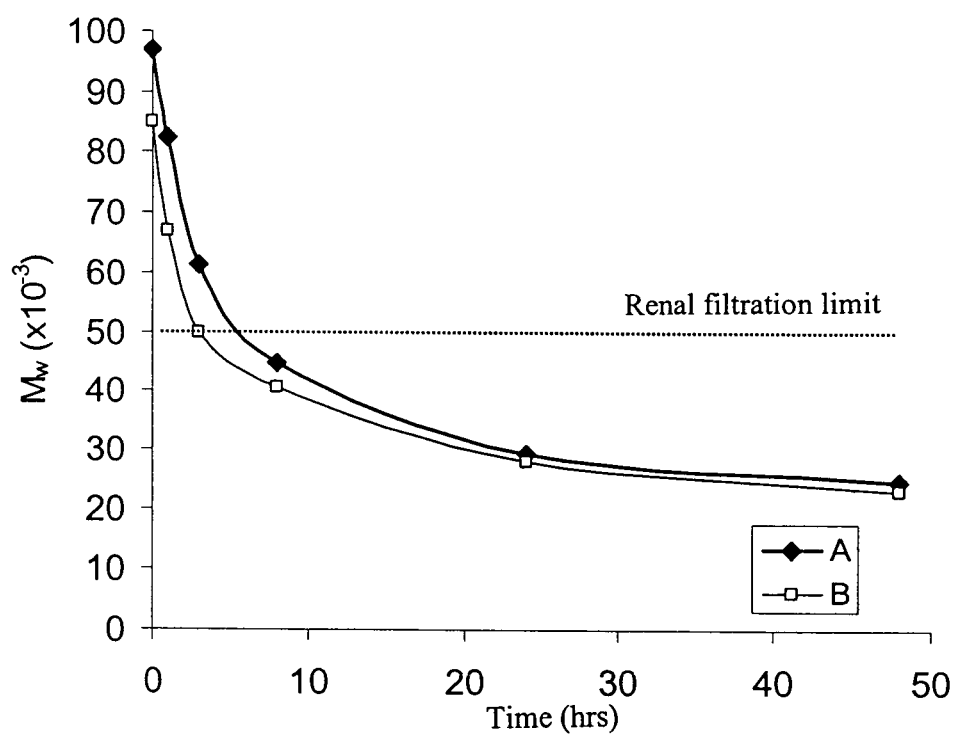
FIG. 3 shows the time dependence of molecular weight of polymeric conjugates during their degradation—A) degradation of Conjugate 1d using the cathepsine B lysosomal enzyme [c(cathepsine B)=$5.10^{-7}$ mol/l]; B) degradation of Conjugate 3a using glutathione [c(glutathione)=$3.10^{-3}$ mol/l].

EXAMPLES OF SYNTHETIC PROCEDURES OF INTERMEDIATE PRODUCTS AND CONJUGATES ACCORDING TO THE INVENTION

Example 1

Synthesis of Monomers and the ABIA-TT Initiator 3,3'-[4,4'-Azobis(4-cyano-4-methyl-1-oxo-butane-4,1-diyl)]bis(thiazolidine-2-thione) (ABIA-TT) was prepared according to a previously described method [Subr 2006]

HPMA was prepared according to a previously described method [Ulbrich a kol. 2000]. Elementary analysis: data counted: 58.8% C, 9.16% H, 9.79% N; data found: 58.98% C, 9.18% H, 9.82% N. The product was chromatographically pure.

6-(Methacryloylamino)hexanoyl-N'-(tert.-butyloxycarbonyl)hydrazine (MA-AH-NHNH-Boc) was prepared according to a previously described method [Ulbrich 2004a]

6-(Methacryloylamino)hexanoylhydrazine ($N^1$-(6-hydrazino-6-oxohexyl)-2-methylacrylamide) (MA-AH-NHNH$_2$) was prepared according to a previously described method [Ulbrich patents, Etrych patent].

MA-GFLG-TT or MA-GFLG-ONp

4-Nitrophenyl ester of N-methacryloylglycyl-DL-fenylalanylleucylglycine (MA-GFLG-ONp) was prepared according to a previously described method [Rejmanova 1977]

Thiazolidine-2-thione of N-methacryloylglycyl-DL-fenylalanylleucylglycine (MA-GFLG-TT) was prepared according to a previously described method [Subr patent]

6-(Methacryloylamino)hexanoylhydrazine-Doxorubicin (MA-AH-NHN=DOX)

6-(Methacryloylamino)hexanoylhydrazine (40 mg, 0.188 mmol) was dissolved in 6 ml of methanol at room temperature. The solution was poured into a reaction vessel in which doxorubicin.HCl (115 mg, 0.198 mmol) was placed and the suspension was stirred vigorously. 310 μl of acetic acid was added to the suspension and the reaction mixture stirred at room temperature for 24 hours. The reaction process was monitored by TLC-Silicagel 60 $F_{254}$ plates (methanol:chloroform:acetic acid 2:8:1, Rf(DOX)=0.75, Rf(MA-AH-NHN=DOX)=0.9). 100 mg of copolymer 1 was then added to the homogenous reaction mixture (to bind the residual free DOX) and the reaction mixture was stirred at room temperature for another 4 hours. The product was purified from polymeric and low-molecular impurities by means of gel chromatography in a column (30 cm×3 cm) filled with Sephadex LH-20 in methanol. The filtrate was concentrated to 2 ml and the product precipitated into 30 ml of diethyl ether. The product was sucked off, washed with a small amount of diethyl ether, and vacuum dried to constant weight. The yield was 110 mg of product (79%) with the melting point of 172 to 175° C. TLC (methanol:chloroform:acetic acid 2:8:1): one stain at Rf=0.9. MALDI-TOF MS: 762 (M+Na).

The poly(HPMA-co-MA-AH-NHNH-Boc)-GLFG-MA methacryloylated macromonomer was prepared by the reaction of the terminal hydrazide or primary amino groups of semitelechelic copolymers (Grafts 2a and 2b) with 4-nitrophenoxy or thiazolidine-2-thione groups of methacryloylated derivatives of biodegradable oligopeptides.

200 mg of the Graft 2a copolymer (0.0125 mmol of NH$_2$ groups) was dissolved in 2 ml of methanol and a solution of 7.7 mg of MA-GFLG-TT (0.0137 mol, 110% in respect of NH$_2$ groups) in 1 ml of methanol was added at room temperature under intensive stirring. After 2 hours the reaction mixture was purified from low-molecular impurities by means of gel chromatography in a column filled with Sephadex LH-20 in methanol under RI detection. The polymeric fraction was captured, concentrated to 3 ml in a vacuum rotary evaporator and the macromonomer was isolated by precipitation into 30 ml of ethyl acetate. The product was dried to constant weight.

Example 2

Synthesis of a Polymeric Precursor—Copolymer 1b—a Copolymer of HPMA with MA-GFLG-TT The poly(HPMA-co-MA-AH-NHNH-Boc-co-MA-GFLG-TT) copolymer was prepared by solution radical copolymerization of HPMA, MA-AH-NHNH-Boc and MA-GFLG-TT in DMSO at 60° C.

465 mg (3.25 mmol) of HPMA, 44.5 mg (0.14 mmol) of MA-AH-NHNH-Boc, 100 mg (0.18 mmol) of MA-GFLG-TT (12.5% by w. of monomers) and 98.3 mg (0.60 mmol) of ABIN (2% by w.) were dissolved in 3.8 ml of DMSO. The ampoule with the polymerization mixture solution was bubbled with nitrogen for 10 minutes, then placed in a thermostat heated to 60° C. for 6 hours. Subsequently, the reaction mixture was precipitated into 80 ml of a mixture of acetone:diethyl ether 3:1 and centrifuged. The polymer was precipitated from methanol into the same mixture, filtered off on the S4 fritted glass and dried to constant weight.

Example 3

Synthesis of a Polymeric Precursor—Copolymer 2a—a Copolymer of HPMA with MA-AH-NHNH$_2$ The poly(HPMA-co-MA-AH-NHNH$_2$) copolymer was prepared by solution radical copolymerization of HPMA and MA-AH-NHNH$_2$ in methanol at 60° C. according to a previously described method [Etrych patent].

Example 4

Synthesis of a Polymeric Precursor—Copolymer 2c—a Copolymer of poly(HPMA-co-MA-AH-NHNH-Boc-co-MA-GFLG-NH$_2$)

The poly(HPMA-co-MA-AH-NHNH-Boc-co-MA-GFLG-NH$_2$) copolymer was prepared by polymer-analogous reaction of the poly(HPMA-co-MA-AH-NHNH-Boc-co-MA-GFLG-TT) copolymer with an excess of ethylene diamine (EDA).

410 mg of the poly(HPMA-co-MA-AH-NHNH-Boc-co-MA-GFLG-TT) polymer (0.10 mmol of TT groups) were dissolved in 6 ml of methanol. 70 μl of EDA (1.05 mmol) were added to the vigorously stirred yellowish solution. After 30 minutes the discolored solution was precipitated into 120 ml of a mixture of acetone:diethyl ether 3:1, precipitated again from methanol into the same mixture and filtered off. The polymer was dried to constant weight.

Example 5

Synthesis of a Polymeric Precursor—Copolymer 3a—a Copolymer of poly(HPMA-co-MA-AH-NHNH$_2$-co-MA-AH-PDS)

The poly(HPMA-co-MA-AH-NHNH$_2$-co-MA-AH-PDS) copolymer was prepared by polymer-analogous reaction of the poly(HPMA-co-MA-AH-NHNH$_2$) copolymer with the SPDP bifunctional agent.

400 mg of the poly(HPMA-co-MA-AH-NHNH$_2$) polymer (0.17 mmol of NHNH$_2$ groups) were dissolved in 7 ml of methanol and a solution of 30 mg of SPDP (0.094 mmol) in 1 ml of methanol was added to the vigorously stirred solution. After 2 hours the reaction mixture was diluted to 15 ml by methanol and the copolymer was purified from low-molecular impurities by means of gel chromatography in a column filled with Sephadex LH-20 in methanol under RI detection. The polymeric fraction was captured, concentrated in a vacuum rotary evaporator to 8 ml and the copolymer was isolated by precipitation into 100 ml of ethyl acetate. The polymer was dried to constant weight.

Example 6

Synthesis of a Polymeric Precursor—Copolymer 3c—a Copolymer of poly(HPMA-co-MA-AH-NHNH-Boc-co-MA-AH-PDS)

The poly(HPMA-co-MA-AH-NHNH-Boc-co-MA-AH-PDS) copolymer was prepared by polymeranalogous reaction of the poly(HPMA-co-MA-AH-NHNH-Boc-co-MA-AH-TT) copolymer with the PDEA bifunctional agent.

20 mg of PDEA.HCl (0.089 mmol) were dissolved in 1 ml of DMSO and 14.5 µl of diisopropylethylamine (0.089 mmol) were added under intensive stirring. After 5 minutes a solution of 300 mg of the poly(HPMA-co-MA-AH-NHNH-Boc-co-MA-AH-TT) polymer (0.073 mmol of TT groups) in 4 ml of DMSO was added to this solution under intensive stirring at room temperature. After 2 hours the reaction mixture was diluted to 15 ml by methanol and the copolymer was purified from low-molecular impurities by means of gel chromatography in a column filled with Sephadex LH-20 in methanol under RI detection. The polymeric fraction was captured, concentrated in a vacuum rotary evaporator to 6 ml and the copolymer isolated by precipitation into 80 ml of a mixture of acetone:diethyl ether 1:3 The product was dried to constant weight.

Example 7

Synthesis of a polymeric Precursor—Copolymer 4b—a Copolymer of poly(HPMA-co-MA-AH-NHNH-Boc-co-MA-GFLG-SH)

The poly(HPMA-co-MA-AH-NHNH-Boc-co-MA-GFLG-SH) copolymer was prepared by polymer-analogous reaction of the poly(HPMA-co-MA-AH-NHNH-Boc-co-MA-GFLG-NH$_2$) copolymer with ITH in a phosphate buffer.

350 mg of the poly(HPMA-co-MA-AH-NHNH-Boc-co-MA-GFLG-NH$_2$) copolymer (0.11 mmol of NH$_2$ groups) were dissolved in 7 ml of phosphate buffer (0.05 M phosphate buffer with 0.1 M NaCl, pH 7.4). 80 mg of ITH (0.58 mmol) were dissolved in 1 ml of distilled water and this solution was added to the copolymer solution under intensive stirring at room temperature. After 30 minutes the reaction mixture was diluted to 20 ml by distilled water and the copolymer purified from low-molecular impurities by means of gel chromatography in a column filled with Sephadex G-25 in distilled water under RI detection. The polymeric fraction was captured and lyophilized in the Lyovac GT-2 lyophilizer.

Example 8

Synthesis of a Polymeric Precursor—Copolymer 4c—a Copolymer of poly(HPMA-co-MA-AH-NHNH$_2$-co-MA-AH-SH)

The poly(HPMA-co-MA-AH-NHNH$_2$-co-MA-AH-SH) copolymer was prepared by reduction of PDS groups of the poly(HPMA-co-MA-AH-NHNH$_2$-co-MA-AH-PDS) copolymer by means of DTT in distilled water.

300 mg of the poly(HPMA-co-MA-AH-NHNH$_2$-co-MA-AH-PDS) copolymer (0.075 mmol of PDS groups) were dissolved in 5 ml of distilled water. 40 mg of DTT (0.26 mmol) were dissolved in 1 ml of distilled water and this solution added to the copolymer solution under intensive stirring at room temperature. After 20 minutes the reaction mixture was diluted to 15 ml by distilled water and the copolymer purified from low-molecular impurities by means of gel chromatography in a column filled with Sephadex G-25 in distilled water under RI detection. The polymeric fraction was captured and lyophilized in the Lyovac GT-2 lyophilizer.

Example 9

Synthesis of a Semitelechelic Polymeric Precursor—Graft 1b—a Copolymer of poly(HPMA-co-MA-AH-NHNH-Boc)-TT The poly(HPMA-co-MA-AH-NHNH-Boc)-TT semi-telechelic copolymer was prepared by solution radical copolymerization of HPMA and MA-AH-NHNH-Boc in DMSO at 60° C. under initiation by the ABIA-TT initiator.

367 mg (2.57 mmol) of HPMA, 70 mg (0.224 mmol) of MA-AH-NHNH-Boc (14% by w. of monomers) were dissolved in 2.7 ml of DMSO and the solution was placed in a polymerization ampoule in which 140 mg (0.290 mmol) of ABIA-TT (4% by w.) were previously weighed. The solution in the ampoule was aerated with nitrogen for 15 minutes, the ampoule was sealed and placed in a thermostat heated to 60° C. The initiator was dissolved after 3 minutes at 60° C. After 6 hours the reaction mixture was precipitated into 80 ml of a mixture of acetone:diethyl ether 2:1. The polymer was dissolved in 4 ml of methanol and precipitated again into 60 ml of the same precipitation mixture. The precipitated copolymer was filtered off on the S4 fritted glass and dried to constant weight.

Example 10

Synthesis of a Semitelechelic Polymeric Precursor—Graft 1c—a Copolymer of poly(HPMA-co-MA-AH-NHNH-Boc)-OSu The poly(HPMA-co-MA-AH-NHNH-Boc)-OSu semi-telechelic copolymer was prepared by solution radical copolymerization of HPMA and MA-AH-NHNH-Boc in ethanol at 50° C. under initiation by the ABIA initiator, followed by activation of terminal carboxyl groups to N-succinimidyl ester.

3.33 g (23.2 mmol) of HPMA, 674 mg (2.16 mmol) of MA-AH-NHNH-Boc (12% by w. of monomers) and 600 mg (2.14 mmol) ABIA (1.8% by w.) were dissolved in 35 ml of ethanol. The solution was placed in a polymerization ampoule and aerated with nitrogen for 15 minutes. The ampoule was then sealed and placed in a thermostat heated to 50° C. After 21 hours the reaction mixture was precipitated into 700 ml of acetone and centrifuged. The copolymer was precipitated again from methanol into the same precipitator, filtered off on the S4 fritted glass and dried to constant weight. In the second step, 400 mg of polymer (0.027 mmol of COOH) were dissolved in 1.75 ml of DMF. 27.5 mg of dicyclohexylcarbodiimide (DCC) (0.133 mmol) and 15.4 mg of N-hydroxysuccinimide (0.133 mmol) were dissolved in 0.2 ml of DMF and added to the stirred copolymer solution cooled to 4° C. (with water-ice mixture). The reaction mixture was stirred for 1.5 hours at 4° C. and for 2 hours at room temperature. The polymer was precipitated into 50 ml of acetone and filtered off on the S4 fritted glass. After being dried to constant weight the sample was stored under argon at −18° C.

Example 11

Synthesis of a Semitelechelic Polymeric Precursor (Synthesis with SPA Transfer)—Graft 1c—a Copolymer of poly(HPMA-co-MA-AH-NHNH-Boc)-OSu The poly(HPMA-co-MA-AH-NHNH-Boc)-OSu semitelechelic copolymer was prepared by precipitation radical copolymerization of HPMA and MA-AH-NHNH-Boc in acetone at 50° C. in the presence of the ABIN initiator and SPA as transfer agent. In the second step, the terminal carboxyl groups were transformed by reaction with DCC and N-hydroxysuccinimide to N-succinimidyl ester.

438 mg (3.07 mmol) of HPMA, 76 mg (0.36 mmol) of MA-AH-NHNH-Boc, 4.6 mg (0.028 mmol) of ABIN and 6 mg (0.057 mmol) of SPA were dissolved in 3.86 ml of acetone and the solution was placed in a polymerization ampoule The solution in the ampoule was aerated with nitrogen for 10 minutes, the ampoule then sealed and placed in a thermostat heated to 50° C. for 19 hours. The separated polymer was filtered off, dissolved in 2 ml of methanol and fractionated in a column filled with Sephadex LH-60 using methanol as the eluent. When the oligomeric fraction was separated the polymer solution was vacuum concentrated and precipitated into a 10-fold excess of a mixture of acetone and diethyl ether (1:1). The polymer was filtered off on the S4 fritted glass and dried to constant weight. In the second step, 340 mg of polymer (0.028 mmol of COOH) were dissolved in 1.6 ml of DMF. 28.5 mg of dicyclohexylcarbodiimide (DCC) (0.138 mmol) and 15.9 mg of N-hydroxysuccinimide (0.138 mmol) were dissolved in 0.2 ml of DMF and added to the stirred copolymer solution cooled to 4° C. The reaction mixture was stirred for 3.5 hours at 4° C. and for 3 hours at room temperature. The polymer was isolated by precipitation into 50 ml of acetone and filtered off on the S4 fritted glass. After being dried to constant weight the sample was stored under argon at −18° C.

Example 12

Synthesis of a Semitelechelic Polymeric Precursor—Graft 1d—a Copolymer of poly(HPMA-co-MA-AH-NHNH-Boc)-GFLG-OSu The poly(HPMA-co-MA-AH-NHNH-Boc)-GFLG-OSu semitelechelic copolymer was prepared though a double step synthesis. In the first step, the N-succinimidyl ester of the poly(HPMA-co-MA-AH-NHNH-Boc)-OSu copolymer reacted with the amino group of the GFLG oligopeptide. In the second step, the terminal carboxyl groups of the prepared poly(HPMA-co-MA-AH-NHNH-Boc)-GFLG-COOH copolymer were transformed to N-succinimidyl ester by reaction with DCC and N-hydroxysuccinimide.

300 mg of the poly(HPMA-co-MA-AH-NHNH-Boc)-OSu copolymer (0.025 mmol of OSu groups) were dissolved in 2 ml of DMF. A solution of 14 mg of the GFLG oligopeptide (0.036 mmol) in 0.2 ml DMF was then added to the solution. The reaction mixture was stirred for 3.5 hours at room temperature. The polymer was isolated by precipitation into 40 ml of acetone and filtered off on the S4 fritted glass. After being dried to constant weight the sample was stored under argon at −18° C. In the second step, 320 mg of polymer (0.027 mmol of COOH) were dissolved in 1.6 ml of DMF. 28.5 mg of dicyclohexylcarbodiimide (DCC) (0.138 mmol) and 15.9 mg of N-hydroxysuccinimide (0.138 mmol) were dissolved in 0.2 ml of DMF and added to the stirred copolymer solution cooled to 4° C. The reaction mixture was stirred for 4 hours at 4° C. and for 3 hours at room temperature. The polymer was isolated by precipitation into 50 ml of acetone and filtered off on the S4 fritted glass. After being dried to constant weight the sample was stored under argon at −18° C.

Example 13

Synthesis of a Semitelechelic Polymeric Precursor (Synthesis with Cysteamine Transfer)—Graft 2a—a Copolymer of poly(HPMA-co-MA-AH-NHNH-Boc)-NH$_2$ The poly(HPMA-co-MA-AH-NHNH-Boc)-NH$_2$ semitelechelic copolymer was prepared by solution radical copolymerization of HPMA and MA-AH-NHNH-Boc in methanol at 50° C. in the presence of the ABIN initiator and cysteamine as transfer agent.

385 mg (2.69 mmol) of HPMA, 76 mg (0.36 mmol) of MA-AH-NHNH-Boc, 1.55 mg (0.0095 mmol) of ABIN and 2.8 mg (0.036 mmol) of cysteamine were dissolved in 4 ml of methanol and the solution was placed in a polymerization ampoule. The solution in the ampoule was aerated with nitrogen for 10 minutes, the ampoule then sealed and placed in a thermostat heated to 50° C. for 24 hours. The polymer was isolated by precipitation into 60 ml of a mixture of acetone and diethyl ether (2:1). The copolymer was filtered off on the S4 fritted glass and precipitated again from methanol (3 ml) into 40 ml of the same precipitation mixture. The polymer was filtered off on the S4 fritted glass and dried to constant weight.

Example 14

Synthesis of a Semitelechelic Polymeric Precursor—Graft 2b—a Copolymer of poly(HPMA-co-MA-AH-NHNH-Boc)-NH$_2$ The poly(HPMA-co-MA-AH-NHNH-Boc)-NH$_2$ semitelechelic copolymer was prepared by polymer-analogous reaction of the poly(HPMA-co-MA-AH-NHNH-Boc)-TT copolymer with ethylene diamine in methanol.

450 mg of the poly(HPMA-co-MA-AH-NHNH-Boc)-TT polymer (0.041 mmol of TT groups) were dissolved in 6 ml of methanol. 30 µl of EDA (0.45 mmol) were added to the vigorously stirred yellowish solution. After 30 minutes the discolored solution was precipitated into 120 ml of a mixture of acetone:diethyl ether 3:1, precipitated again from methanol into the same mixture and filtered off. The polymer was dried to constant weight.

Example 15

Synthesis of a Semitelechelic Polymeric Precursor—Graft 3a—a Copolymer of poly(HPMA-co-MA-AH-NHNH-Boc)-PDS The poly(HPMA-co-MA-AH-NHNH-Boc)-PDS semitelechelic copolymer was prepared by polymer-analogous reaction of the poly(HPMA-co-MA-AH-NHNH-Boc)-TT copolymer with the PDEA bifunctional agent in DMSO.

10 mg of PDEA.HCl (0.045 mmol) were dissolved in 0.5 ml of DMSO and 7.3 µl of diisopropylethylamine (0.045 mmol) were added under intensive stirring. After 5 minutes a solution of 400 mg of the poly(HPMA-co-MA-AH-NHNH-Boc)-TT copolymer (0.036 mmol of TT groups) in 5 ml of DMSO was added to this solution under intensive stirring at room temperature. After 2 hours the reaction mixture was diluted to 15 ml by methanol and the copolymer was purified from low-molecular impurities by means of gel chromatography in a column filled with Sephadex LH-20 in methanol (RI detection). The polymeric fraction was captured, concentrated in a vacuum rotary evaporator to 6 ml and the copolymer isolated by precipitation into 80 ml of a mixture of acetone:diethyl ether 3:1. The product was dried to constant weight.

Example 16

Synthesis of a Semitelechelic Polymeric Precursor—Graft 3b—a Copolymer of poly(HPMA-co-MA-AH-NHNH-Boc)-PDS The poly(HPMA-co-MA-AH-NHNH-Boc)-PDS semitelechelic copolymer was prepared by polymer-analogous reaction of the poly(HPMA-co-MA-AH-NHNH-Boc)-$NH_2$ copolymer with the SPDP bifunctional agent in methanol.

300 mg of the poly(HPMA-co-MA-AH-NHNH-Boc)-$NH_2$ polymer (0.025 mmol of $NHNH_2$ groups) were dissolved in 4 ml of methanol and a solution of 11 mg of SPDP (0.035 mmol) in 1 ml was added to the intensively stirred solution. After 2 hours the reaction mixture was diluted with methanol to 15 ml and the copolymer was purified from low-molecular impurities by means of gel chromatography in a column filled with Sephadex LH-20 in methanol under RI detection. The polymeric fraction was captured, concentrated in a vacuum rotary evaporator to 8 ml and the copolymer isolated by precipitation into 100 ml of ethyl acetate. The product was dried to constant weight.

Example 17

Synthesis of a Semitelechelic Polymeric Precursor—Graft 4a—a Copolymer of poly(HPMA-co-MA-AH-NHNH-Boc)-SH The poly(HPMA-co-MA-AH-NHNH-Boc)-SH semitelechelic copolymer was prepared by polymer-analogous reaction of the (HPMA-co-MA-AH-NHNH-Boc)-$NH_2$ copolymer with ITH in phosphate buffer.

250 mg of the poly(HPMA-co-MA-AH-NHNH-Boc)-$NH_2$ (0.021 mmol of $NH_2$ groups) copolymer were dissolved in 5 ml of phosphate buffer (0.05 M phosphate buffer with 0.1 M NaCl, pH 7.4). 16 mg of ITH (0.116 mmol) were dissolved in 0.5 ml of distilled water and this solution was added to the copolymer solution under intensive stirring at room temperature. After 25 minutes the reaction mixture was diluted to 15 ml by distilled water and the copolymer purified from low-molecular impurities by means of gel chromatography in a column filled with Sephadex G-25 in distilled water under RI detection. The polymeric fraction was captured and lyophilized in the Lyovac GT-2 lyophilizer.

Example 18

Synthesis of a Semitelechelic Polymeric Precursor—Graft 4b—a Copolymer of poly(HPMA-co-MA-AH-NHNH-Boc)-SH The poly(HPMA-co-MA-AH-NHNH-Boc)-SH semitelechelic copolymer was prepared by reduction of PDS groups of the poly(HPMA-co-MA-AH-NHNH-Boc)-PDS copolymer with the help of DTT in distilled water.

300 mg of the poly(HPMA-co-MA-AH-$NHNH_2$)-PDS copolymer (0.022 mmol of PDS groups) were dissolved in 5 ml of distilled water. 20 mg of DTT (0.13 mmol) were dissolved in 1 ml of distilled water and this solution added to the copolymer solution under intensive stirring at room temperature. After 20 minutes the reaction mixture was diluted to 15 ml by distilled water and the copolymer purified from low-molecular impurities by means of gel chromatography in a column filled with Sephadex G-25 in distilled water under RI detection. The polymeric fraction was captured and lyophilized in the Lyovac GT-2 lyophilizer.

Example 19

Synthesis of a Polymeric Conjugate—Conjugate 1d—a Copolymer of poly(HPMA-co-MA-AH-$NHNH_2$-MA-AH-NHN=DOX-co-MA-GFLG-NH—)-graft-[(GFLG)-poly(HPMA-co-MA-AH-$NHNH_2$-co-MA-AH-NHN=DOX)]

The poly(HPMA-co-MA-AH-$NHNH_2$-co-MA-AH-NHN=DOX-co-MA-GFLG-NH—)-graft-[(GFLG)-poly(HPMA-co-MA-AH-$NHNH_2$-co-MA-AH-NHN=DOX)] polymeric conjugate was prepared by reaction of the amino groups of the poly(HPMA-co-MA-AH-NHNH-Boc-co-MA-GFLG-$NH_2$) copolymer with the TT groups of the poly(HPMA-co-MA-AH-NHNH-Boc)-TT copolymer, followed by protection of the hydrazide groups by trifluoracetic acid (TFA) and binding of DOX in methanol catalyzed by acetic acid.

180 mg of poly(HPMA-co-MA-AH-NHNH-Boc)-TT (0.015 mmol of TT) were dissolved in 3 ml of DMSO and added at room temperature to a stirred solution of 70 mg of poly(HPMA-co-MA-AH-NHNH-Boc-co-MA-GFLG-$NH_2$) (0.017 mmol of $NH_2$) in 2 ml of DMSO. After 2.5 hours of the room temperature reaction the solution was precipitated to 50 ml of a mixture of ethyl acetate:diethyl ether 3:1 and filtered off on the S4 fritted glass. The grafted copolymer was dissolved in 4 ml of methanol, precipitated again to the ethyl acetate:diethyl ether mixture, filtered and dried to constant weight. When removing the protective Boc groups 220 mg of the grafted copolymer were dissolved in 6 ml of a mixture of TFA:triisopropylsilane:water 95:2.5:2.5. After 15 minutes the mixture was repeatedly evaporated with methanol (in 5-fold excess) in a vacuum evaporator using a water aspirator vacuum until crystals were formed. The product was dissolved in water and the water solution pH was increased to pH=7-8. The copolymer was purified from low-molecular impurities by means of gel chromatography in a column filled with Sephadex G-25 in distilled water under RI detection. The polymeric fraction was captured and lyophilized in the Lyovac GT-2 lyophilizer. When binding DOX to the grafted copolymer 200 mg of copolymer were dissolved in 2 ml of methanol and the solution was poured in a thermo-regulated cell where 20 mg of DOX.HCl (0.034 mmol) were placed. The non-homogenous suspension was stirred in dark at 25° C. and after 1 minute 100 µl of acetic acid were added. The suspension gradually dissolved and after 23 hours of reaction the polymeric product was purified from low-molecular impurities and any residual free drug by means of gel chromatography in a column filled with Sephadex LH-20 in methanol. The polymeric fraction was captured, concentrated to 3 ml in a vacuum rotary evaporator and the copolymer was isolated by precipitation into 30 ml of ethyl acetate. The product was dried to constant weight.

Example 20

Synthesis of a Polymeric Conjugate—Conjugate 2—a Copolymer of poly(HPMA-co-MA-AH-NHNH$_2$-co-MA-AH-NHN=DOX-co-MA-GFLG-NH—)-graft-[(GFLG)-poly(HPMA-co-MA-AH-NHNH$_2$-MA-AH-NHN=DOX)]

The poly(HPMA-co-MA-AH-NHNH$_2$-co-MA-AH-NHN=DOX-co-MA-GFLG-NH—)-graft-[(GFLG)-poly(HPMA-co-MA-AH-NHNH$_2$-MA-AH-NHN=DOX)] polymeric conjugate was prepared by reaction of the ONp groups of the poly(HPMA-co-MA-AH-NHNH-Boc-co-MA-GFLG-ONp) copolymer with the hydrazide groups of the poly(HPMA-co-MA-AH-NHNH-Boc)-NHNH$_2$ copolymer, followed by protection of the hydrazide groups by trifluoracetic acid (TFA) and binding of DOX in methanol catalyzed by acetic acid.

250 mg of poly(HPMA-co-MA-AH-NHNH-Boc)-NHNH$_2$ (0.019 mmol of TT) were dissolved in 4 ml of DMSO and added at room temperature to a stirred solution of 90 mg of poly(HPMA-co-MA-AH-NHNH-Boc-co-MA-GFLG-ONp) (0.021 mmol of NH$_2$) in 2.5 ml of DMSO. After 3 hours of the room temperature reaction the solution was precipitated into 50 ml of a mixture of acetone:diethyl ether 3:1 and filtered off on the S4 fritted glass. The grafted copolymer was dissolved in 5 ml of methanol, precipitated again to the ethyl acetate:diethyl ether mixture, filtered and dried to constant weight. The removal of the protective Boc groups, as well as the binding of the drug to the grafted copolymer was carried out analogously as in Example 19.

Example 21

Synthesis of a Polymeric Conjugate—Conjugate 3a—a Copolymer of poly(HPMA-co-MA-AH-NHNH$_2$-co-MA-AH-NHN=DOX-co-MA-AH-SS—)-graft-[(SS)-poly(HPMA-co-MA-AH-NHNH$_2$-MA-AH-NHN=DOX)]

The poly(HPMA-co-MA-AH-NHNH$_2$-co-MA-AH-NHN=DOX-co-MA-AH-SS—)-graft-[(SS)-poly(HPMA-co-MA-AH-NHNH$_2$-MA-AH-NHN=DOX)] polymeric conjugate was prepared by reaction of the PDS groups of the poly(HPMA-co-MA-AH-NHNH$_2$-co-MA-AH-PDS) copolymer with the sulfhydryl groups of the poly(HPMA-co-MA-AH-NHNH-Boc)-SH copolymer, followed by protection of the hydrazide groups by trifluoracetic acid (TFA) and binding of DOX in methanol catalyzed by acetic acid.

330 mg of poly(HPMA-co-MA-AH-NHNH-Boc)-SH (0.021 mmol of SH groups) were dissolved in 7 ml of phosphate buffer (0.05 M phosphate buffer with 0.1 M NaCl, 0.01 M ethylenediaminetetraacetic acid (EDTA), pH 7.4) and added at room temperature to a stirred solution of 108 mg of poly(HPMA-co-MA-AH-NHNH$_2$-co-MA-AH-PDS) (0.025 mmol of PDS groups) in 2.5 ml of the same buffer. After 3 hours of the room temperature reaction the grafted copolymer was purified from low-molecular impurities by means of gel chromatography in a column filled with Sephadex G-25 in distilled water under RI detection. The polymeric fraction was captured and lyophilized in the Lyovac GT-2 lyophilizer. The removal of the protective Boc groups, as well as the binding of the drug to the grafted copolymer was carried out analogously as in Example 19.

Example 22

Synthesis of a Polymeric Conjugate—Conjugate 3a—a Copolymer of poly(HPMA-co-MA-AH-NHNH$_2$-co-MA-AH-NHN=DOX-co-MA-AH-SS—)-graft-[(SS)-poly(HPMA-co-MA-AH-NHNH$_2$-MA-AH-NHN=DOX)]

The poly(HPMA-co-MA-AH-NHNH$_2$-co-MA-AH-NHN=DOX-co-MA-AH-SS—)-graft-[(SS)-poly(HPMA-co-MA-AH-NHNH$_2$-MA-AH-NHN=DOX)] polymeric conjugate was prepared by reaction of the SH groups of the poly(HPMA-co-MA-AH-NHNH-Boc-co-MA-AH-SH) with the PDS groups of the poly(HPMA-co-MA-AH-NHNH-Boc)-PDS copolymer, followed by protection of the hydrazide groups by trifluoracetic acid (TFA) and binding of DOX in methanol catalyzed by acetic acid.

280 mg of poly(HPMA-co-MA-AH-NHNH-Boc)-PDS (0.019 mmol of PDS groups) were dissolved in 6 ml of phosphate buffer (0.05 M phosphate buffer with 0.1 M NaCl, 0.01 M ethylenediaminetetraacetic acid (EDTA), pH 7.4) and added at room temperature to a stirred solution of 95 mg of poly(HPMA-co-MA-AH-NHNH-Boc-co-MA-AH-SH) (0.024 mmol of SH groups) in 2.5 ml of the same buffer. After 3 hours of the room temperature reaction the grafted copolymer was purified from low-molecular impurities by means of gel chromatography in a column filled with Sephadex G-25 in distilled water under RI detection. The polymeric fraction was captured and lyophilized in the Lyovac GT-2 lyophilizer. The removal of the protective Boc groups, as well as the binding of the drug to the grafted copolymer was carried out analogously as in Example 19.

Example 23

Synthesis of a Polymeric Conjugate—Conjugate 5—a Copolymer of poly(HPMA-co-MA-AH-NHNH$_2$-co-MA-AH-NHN=DOX-co-MA-GFLG-NH—)-graft-[(GFLG)-poly(HPMA-co-MA-AH-NHNH$_2$-MA-AH-NHN-DOX)]

The poly(HPMA-co-MA-AH-NHNH$_2$-co-MA-AH-NHN=DOX-co-MA-GFLG-NH—)-graft-[(GFLG)-poly(HPMA-co-MA-AH-NHNH$_2$-MA-AH-NHN=DOX)] polymeric conjugate was prepared by solution radical copolymerization of HPMA, MA-AH-NHNH$_2$ and poly (HPMA-co-MA-AH-NHNH-Boc)-GLFG-MA in methanol at 60° C.

465 mg (3.25 mmol) of HPMA, 44.5 mg (0.20 mmol) of MA-AH-NHNH$_2$, 950 mg (0.076 mmol) of poly(HPMA-co-MA-AH-NHNH-Boc)-GLFG-MA and 98.3 mg (0.60 mmol) of ABIN were dissolved in 9 ml of methanol. The ampoule with the polymerization mixture solution was aerated with nitrogen for 10 minutes, then sealed and placed in a thermostat heated to 60° C. for 24 hours. The reaction mixture was then precipitated into 100 ml of a mixture of acetone:diethyl ether 3:1 and centrifuged. The polymer was precipitated again from methanol into the same mixture, filtered off on the S4 fritted glass and dried to constant weight. The removal of the protective Boc groups, as well as the binding of the drug to the grafted copolymer was carried out analogously as in Example 19.

Example 24

Release of Doxorubicin from Grafted Polymeric Conjugates

The amounts of doxorubicin released from grafted polymeric conjugates after their incubation in a phosphate buffer with pH 5.0 (0.1 M phosphate buffer containing 0.05 M NaCl), modeling the intracellular environment, and in a phosphate buffer with pH 7.4, modeling the bloodstream environment, were measured. The amount of released DOX in the incubation solution was determined by means of HPLC (Shimadzu). In predetermined intervals, 50 μl of the incubation solution were sampled and analyzed in a TSKGel G 3000xl column, isocratic flow 0.5 ml/min of the mobile phase composed of a mixture of methanol:acetate buffer of pH 6.5 (80:20% by vol.). The amount of DOX was calculated from the areas of peaks of free and bound DOX (UV-VIS detection at 488 nm). After incubation of the conjugates (5 mg/ml concentration) in the physiologic environment at 36° C. (phosphate buffer, pH 7.4), only a small amount of the drug is released (up to 8%/24 hours) (FIG. 33); on the contrary, the release rate of DOX from the grafted polymeric conjugates, and hence the activation rate of the cytotoxic drug, is considerable in the slightly acidic environment at pH 5.0 (FIG. 35). At pH 7.4 and pH 5 the rates of drug release from the grafted polymeric conjugates are fully comparable with those detected for the hydrazone conjugates prepared from linear copolymers only [Etrych patent].

Example 25

Degradation of Grafted Polymeric Conjugates by Glutathione or Cathepsine B into Degradation Products Excludable from the Body The degradation experiments were carried in a phosphate buffer (0.1 M phosphate buffer containing 0.05 M NaCl, pH 6) in the presence of cathepsine B or glutathione in the role of degradation agents, i.e. in the environment modeling intracellular environment (cytoplasm, endosome and secondary lysosome). The grafted polymeric conjugates were dissolved in the phosphate buffer in concentration of 50 mg/ml and immediately before the solutions were placed in a thermostat (37° C.) a stock solution of cathepsine B or glutathione was added to the solutions so that the final concentration of these agents in the incubation medium was $5.10^{-7}$ mol/l and $3.10^{-3}$ mol/l for cathepsine and glutathione, respectively. In predetermined intervals aliquot parts (200 μl) were sampled from the incubation solutions. The samples were desalinated in the PD-10 columns and lyophilized. The molecular weight of the degradation products was measured using the Shimadzu SIL-HT liquid chromatograph fitted with a differential refractometer (Shimadzu RID-10A) and multiangle light dispersion detector (DAWN EOS, Wyatt Technology, USA). The analysis was carried out in a Superose™ 6 column (300×10 mm) (Amersham Bioscience). 0.3 M acetate buffer (CH$_3$COONa/CH$_3$COOH; pH=6.5; 0.5 g/l NaN$_3$) with a flow rate of 0.5 ml/min was used as the mobile phase. The molecular weight and polydispersity of the copolymer was calculated using the Astra software. (Wyatt Technology, USA).

The conjugates containing the GlyPheLeuGly (SEQ ID. NO. 3) enzymatically degradable sequences (Conjugate 1d) were degraded in the course of 24 hours by cathepsine B to degradation products whose molecular weight was below the renal filtration limit (FIG. 37). In a solution containing glutathione ($3.10^{-3}$ mol/l) rapid degradation of the grafted conjugates containing disulfide bridges was detected. These grafted conjugates were degraded after 24 hours into polymeric degradation products with a molecular weight below the renal filtration limit (~25,000 g/mol).

Example 26

Example of In Vitro Biological Activity of Grafted Conjugates of Doxorubicin During Incubation with the Cells of Various Tumor Lines

TABLE 1

Cytotoxicity of grafted polymers, comparison with Hydrazone

| Sample No.: | Structure: | EL4 | 38C13 | SW620 | ConA | 3T3 | Raji | Jurkat |
|---|---|---|---|---|---|---|---|---|
| B-578 | P-Acap-Dox (Hydrazone) | <0.016 0.342 0.035 | 0.004 <0.016 | 0.034 | 0.09 | 0.019 | <0.016 | 0.258 |
| B-624 | P-AA-NH-N=Dox\ GFLG-OH | 0.152 0.290 | 0.0094 0.0008 | 0.900* 0.040 | 0.051 0.213 | 0.045 0.04 | 0.003 0.0107 | 0.835* 0.461 |
| B-599 | P-AK-HN-N=Dox\ gr-GFLG-P-NHN=Dox | 0.557 | <0.016 | | | | | |
| B-613 | P-AK-NH-N=Dox\ gr-S-S-P-AA-NH-N=Dox | 0.017 | 0.01 | 0.019 | 0.098 | | | |

TABLE 1-continued

Cytotoxicity of grafted polymers, comparison with Hydrazone

| Sample No.: | Structure: | EL4 | 38C13 | SW620 | ConA | 3T3 | Raji | Jurkat |
|---|---|---|---|---|---|---|---|---|
| | Dox | 0.015 | 0.0005 | 0.003 | 0.029 | 0.009 | 0.0005 | 0.119* |
| | | 0.007 | 0.0002 | | 0.008 | 0.003 | 0.0014 | 0.119 |

Both types of Dox grafted conjugates (those with grafts attaches by an enzymatically cleavable bond and with a reductively cleavable bond) were tested in vitro using a scale of tumor lines of both mouse (EL 4; 38C13; 3T3; BCL1) and human origin (SW 620). It was found out that the $IC_{50}$ value of the conjugates in all the tested lines was 5-10 times lower than that of free unmodified doxorubicin. All the tested lines are very sensitive to the conjugates but it depends on their origin. The most sensitive one was the line of mouse B cellular lymphoma 38C13. The lines of human colorectal carcinoma and mouse fibrosarcoma were less sensitive, followed by the line of mouse B leukemia. Mouse T cellular lymphoma was the least sensitive one.

Example 27

Example of In Vivo Biological Activity of Grafted Conjugates of Doxorubicin in Mice Inoculated by T Cellular Lymphoma EL4

Figure 4:
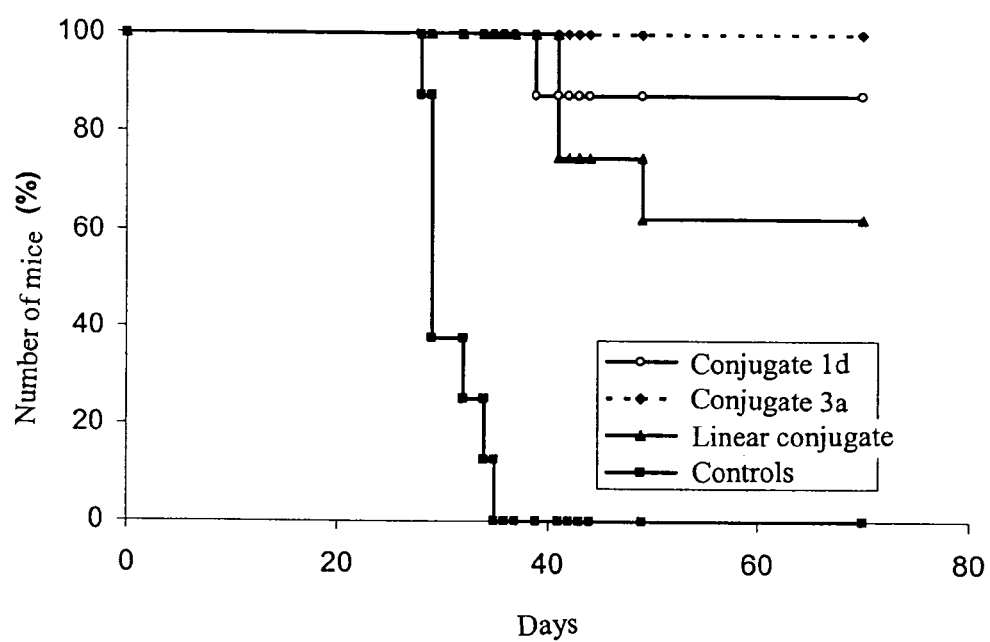
FIG. 4 shows a graph of survival rate of B/6 mice inoculated with the EL 4 mouse lymphoma treated by DOX grafted conjugates after intravenous administration of one dose of 15 mg/kg of DOX equivalent in a therapeutic mode of drug administration.

The in vivo experiments involved a model of mouse T cellular lymphoma EL4, the experimental animals were mice (males) of the B/6 species that were subcutaneously implanted with $10^5$ tumor cells on day 0. The conjugates were applied intravenously in a dose of 1×15 mg/kg of DOX equivalent. This single application was carried out on the ninth day after the tumor cells transplantation, i.e. at a time when the tumor was palpable, about approx. 400 mm³ in size. As early as on the third day after the first application all experimental groups showed significantly slowed growth of tumors compared with controls. Both grafted conjugates (Conjugate 1d and Conjugate 3a) showed a very significant anticancer effect. In both cases the tumor growth was suppressed and in most testing animals the tumor faded out. After the application of Conjugate 3a (SS bridge) 100% of mice were surviving on the 70th day of tumor cells application, which was the end of the experiment. In case of Conjugate 1d 88% of the laboratory animals survived to the 70th day when the experiment was ended. In both experimental groups treated with samples of grafted conjugates significant recession of the tumor was obvious after the conjugates were administered, no weight decrease as a sign of toxicity was observed. In control treatment with a linear soluble conjugate five mice of eight were cured. All of these control animals died; the shortest and longest survival intervals were 28 days and 35 days, respectively. Examples of the in vivo test results are shown in FIG. 4 and table 1 (LTS—long term survivors).

TABLE 1

Survival of B/6 mice inoculated with mouse lymphoma EL 4 (day 0, $10^5$ cells, s.c.) treated with DOX grafted conjugates after intravenous application of one dose of 15 mg/kg DOX equivalent in a therapeutic mode of drug administration (day 9).

| Conjugate 1d | Conjugate 3a | Linear conjugate | Controls |
|---|---|---|---|
| 39 | LTS | 41 | 28 |
| LTS | LTS | 41 | 29 |
| LTS | LTS | 49 | 29 |
| LTS | LTS | LTS | 29 |
| LTS | LTS | LTS | 29 |
| LTS | LTS | LTS | 32 |
| LTS | LTS | LTS | 34 |
| LTS | LTS | LTS | 35 |

The linear conjugate is a control »classic" soluble ungrafted conjugate. The days mean particular days of animal death, LTS means surviving animals without a palpable tumor.

References

Bae, Y. S.; Fukushima, S.; Harada, A.; Kataoka, K. pH responsive drug-loaded polymeric micelles: Intracellular drug release correlated with in vitro cytotoxicity on human small cell lung cancer SBC-3. 2003. Salt Lake City, Utah, U.S.A. Winter Symposium and 11th International Symposium on Recent Advances in Drug Delivery Systems. 2003.

Bronich, T. K.; Nehls, A.; Eisenberg, A.; Kabanov, V. A.; Kabanov, A. V. *Colloids Surf. B* 1999, 16, 243-251.

R. Duncan, J. B. Lloyd, J. Kopecek, P. Rejmanova, J. Strohalm, K. Ulbrich, B. Rihova, V. Chytry: Synthetic Polymeric Drugs (1985). Czech. PV 0095/85, Australia 589587, Canada 130053, Denmark 164485, Europe 0187547, U.S. Pat. No. 5,037,883, Japan 000137/86

Etrych, T., Jelinkova, M., Rihova, B. and Ulbrich K., New HPMA copolymers containing doxorubicin bound via pH sensitive linkage. Synthesis, in vitro and in vivo biological properties. *J. Controlled Release* 73, 89-102 (2001).

T. Etrych, P. Chytil, M. Jelinkova, B. Rihova, K. Ulbrich, Synthesis of HPMA Copolymers Containing Doxorubicin Bound via a Hydrazone Linkage. Effect of Spacer on Drug Release and in vitro Cytotoxicity. *Macromolecular Biosci.* 2, 43-52 (2002)

Etrych T., Chytil P., Pechar M., Studenovsky M., Rihova B., Ulbrich K.: Method of Preparation of Polymeric Conjugates of Doxorubicin with pH-controlled Drug Release, CZ PV 2005-558

Kataoka, K.; Harada, A.; Nagasaki, Y. *Adv. Drug Delivery Rev.* 2001, 47, 113-131.

Kopecek J., Kopeckova P., Minko T., Lu Z., HPMA Copolymer-Anticancer Drug Conjugates: Design, Activity and Mechanism of Action. *Europ. J. Pharm. Biopharm.* 50, 61-81 (2000)

Kopecek, J., Kopeckova, P., Minko, T., Lu, Z. R., Peterson, C. M. (2001) "Water soluble polymers in tumor targeted delivery". *J. Controlled Release* 74, 165-173.

F. Kratz, U. Beyer, M. T. Schutte, Drug-polymer conjugates containing acid-cleavable bonds, *Crit. Rev. Ther. Drug Carrier Syst.* 16 (1999) 245-288.

Maeda, H., J. Wu, T. Sawa, Y. Matsumura, and K. Hori. 2000. Tumor vascular permeability and the EPR effect in macromolecular therapeutics: a review. *J Control Release* 65:271-284.

Maeda, H. 2001. The enhanced permeability and retention (EPR) effect in tumor vasculature: the key role of tumor-selective macromolecular drug targeting. *Adv Enzyme Regul* 41:189-207.

Y. Noguchi, J. Wu, R. Duncan, J. Strohalm, K. Ulbrich, T. Akaike, H. Maeda, *Jpn. J. Cancer Res.* 89, 307-314 (1998)

P. Rejmanova, J. Labsky, J. Kopecek, Aminolyses of Monomeric and Polymeric 4-nitrophenyl Esters of N-Methacroylamino Acids, *Makromol. Chem.* 178, 2159-2168 (1977)

B. Rihova, M. Jelinkova, J. Strohalm, V. Subr, D. Plocova, O. Hovorka, M. Novak, D. Plundrova, Y. Germano, K. Ulbrich, Polymeric Drugs Based on Conjugates of Synthetic and Natural Macromolecules II. Anti-cancer Activity of antibody or (Fab')$_2$-targeted Conjugates and Combined Therapy with Immunomodulators. *J. Controlled Rel.* 64, 241-261 (2000)

L. W. Seymour, Y. Miyamoto, H. Maeda, M. Brereton, J. Strohalm, K. Ulbrich, R. Duncan, *Europ. J. Cancer* 31A, 766-770 (1995)

V. Subr, K. Ulbrich, B. Rihova, Reactive polymers and copolymers based on N-(2-hydroxypropyl)methacrylamide, a method of their preparation and their use for synthesis of polymer drugs, for modification of biologically active proteins and for gene transport systems, PV 1950/03

V. Subr, C. Konak, R. Laga, K. Ulbrich, Coating of DNA/poly (L-lysine) complexes by covalent attachment of poly[N-(2-hydroxypropyl)methacrylamide], *Biomacromolecules* 7, 122-130 (2006)

K. Ulbrich, V. Subr, J. Strohalm, D. Plocova, M. Jelinkova, B. Rihova, Polymeric Drugs Based on Conjugates of Synthetic and Natural Macromolecules I. Synthesis and Physico-chemical Characterisation. *J. Controlled Rel.* 64, 63-79 (2000)

K. Ulbrich, T. Etrych, P. Chytil, M. Jelinkova, B. Rihova, Antibody-Targeted Polymer-Doxorubicin Conjugates with pH-Controlled Activation, *J. Drug Targeting* 12(8) (2004) 477-489]. (A)

K. Ulbrich, V. Subr, Polymeric Anticancer Drugs with pH-Controlled Activation, *Adv. Drug Delivery Rev.* 56/7, 1025-1052 (2004) (B)

K. Ulbrich, T. Etrych, B. Rihova, M. Jelinkova, M. Kovar: pH-sensitive Polymeric Conjugates of an Anthracycline Cancerostatic for Targeted Therapy. CZ 293787, CZ 293886

Yokoyama, M.; Okano, T.; Sakurai, Y.; Fukushima, S.; Okamoto, K.; Kataoka, K. *J. Drug Targeting* 1999, 7, 171-186.

Yoo, H. S.; Lee, E. A.; Park, T. G. *J. Controlled Release* 2002, 82, 17-27.

---

The invention claimed is:

1. A polymeric drug having a main chain and a graft chain said graft being bound to the main chain by a bond, which is stable in the body or by a bond cleavable in the body or by a combination thereof, wherein the molecular weight of the main chain range is from 10,000 to 50,000 g/mol, and the molecular weight of the grafts range is from 5,000 to 50,000 g/mol, and wherein the total molecular weight of the grafted polymer ranges from 50,000 to 400,000 g/mol; and wherein the polymeric drug is of structure 1a:

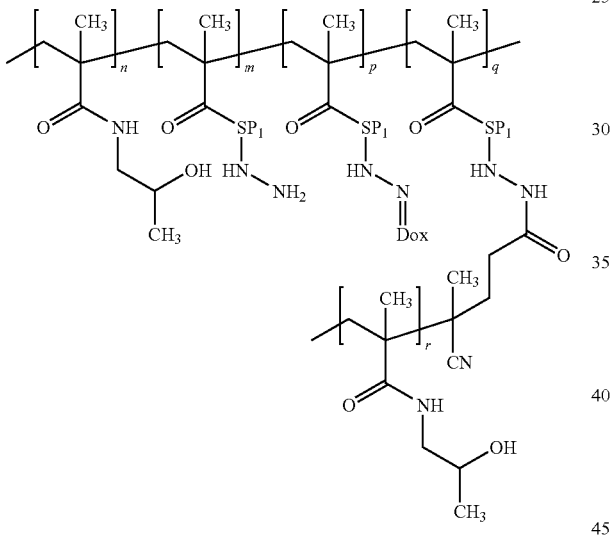

Wherein Dox is doxorubicin, n ranges from 40 to 335, m from 0 to 85, p from 1 to 20, q from 1 to 10 and r from 34 to 350; SP1 is an aminoacyl, glycyl, glycylglycyl, B-alanyl, 6-aminohexanoyl (AH) or 4-aminobenzoyl or a combined acyl derivative from the oligopeptides GlyPheGly (SEQ ID. NO. 2), GlyLeuGly (SEQ ID. NO. 1), GlyLeuPheGly (SEQ ID. NO. 4) or GLyPheLeuGly (SEQ ID. N). 3) or any combination thereof.

2. The polymeric drug according to claim 1, wherein the graft is bound to the main chain by a bond cleavable in a tumor cell, enzymatically and/or reductively.

3. The polymeric drug according to claim 1, wherein the cancerostatic content ranges from 1 to 25% by weight.

4. A pharmaceutical composition containing, as the active component, a substance according to claim 1.

5. A method for treating a solid tumor comprising the step of administering the pharmaceutical composition of claim 4.

6. A method for treating lymphoma or leukemia comprising the step of administering the pharmaceutical composition of claim 4.

* * * * *